US011521343B2

(12) United States Patent
Potter et al.

(10) Patent No.: US 11,521,343 B2
(45) Date of Patent: Dec. 6, 2022

(54) GRAPHICS MEMORY SPACE FOR SHADER CORE

(71) Applicant: Apple Inc., Cupertino, CA (US)

(72) Inventors: Terence M. Potter, Austin, TX (US); Yoong Chert Foo, London (GB); Ali Rabbani Rankouhi, St Albans (GB); Justin A. Hensley, Mountain View, CA (US); Jonathan M. Redshaw, St Albans (GB)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/103,462

(22) Filed: Nov. 24, 2020

(65) Prior Publication Data

US 2022/0148249 A1 May 12, 2022

Related U.S. Application Data

(60) Provisional application No. 63/058,868, filed on Jul. 30, 2020.

(51) Int. Cl.
*G06F 15/16* (2006.01)
*G06T 15/06* (2011.01)
(Continued)

(52) U.S. Cl.
CPC .......... *G06T 15/06* (2013.01); *G06F 9/3887* (2013.01); *G06F 9/4881* (2013.01);
(Continued)

(58) Field of Classification Search
CPC ......... G06T 1/20; G06T 15/005; G09G 5/363; G09G 5/393; G06F 3/14
(Continued)

(56) References Cited

U.S. PATENT DOCUMENTS 8,203,559 B2   6/2012   Peterson et al.
8,212,816 B1   7/2012   Hoberock et al.
(Continued)

FOREIGN PATENT DOCUMENTS

CN   102037497 A   4/2011
CN   110827387 A   2/2020
(Continued)

OTHER PUBLICATIONS

European Search Report in Appl. No. 21187498.7 dated Dec. 20, 2021, 15 pages.
(Continued)

*Primary Examiner* — Gordon G Liu
(74) *Attorney, Agent, or Firm* — Kowert, Hood, Munyon, Rankin & Goetzel, P.C.; Michael B. Davis; Dean M. Munyon

(57) ABSTRACT

Disclosed techniques relate to memory space management for graphics processing. In some embodiments, first and second graphics cores are configured to execute instructions for multiple threadgroups. In some embodiments, the threads groups include a first threadgroup with multiple single-instruction multiple-data (SIMD) groups configured to execute a first shader program and a second threadgroup with multiple SIMD groups configured to execute a second, different shader program. Control circuitry may be configured to provide access to data stored in memory circuitry according to a shader memory space. The shader memory space may be accessible to threadgroups executed by the first graphics shader core, including the first and second threadgroups, but is not accessible to threadgroups executed by the second graphics shader core. Disclosed techniques may reduce latency, increase bandwidth available to the shader, reduce coherency cost, or any combination thereof.

20 Claims, 27 Drawing Sheets

(51) Int. Cl.
*G06T 15/00* (2011.01)
*G06F 9/48* (2006.01)
*G06F 9/50* (2006.01)
*G06T 1/20* (2006.01)
*G06F 16/22* (2019.01)
*G06F 30/31* (2020.01)
*G06F 9/38* (2018.01)
*G06T 1/60* (2006.01)
*G06T 17/10* (2006.01)
*G16H 40/67* (2018.01)
*G06Q 10/10* (2012.01)
*G06Q 50/04* (2012.01)

(52) U.S. Cl.
CPC .......... *G06F 9/5016* (2013.01); *G06F 9/5027* (2013.01); *G06F 16/2246* (2019.01); *G06F 30/31* (2020.01); *G06T 1/20* (2013.01); *G06T 1/60* (2013.01); *G06T 15/005* (2013.01); *G06Q 10/101* (2013.01); *G06Q 50/04* (2013.01); *G06T 17/10* (2013.01); *G06T 2210/12* (2013.01); *G06T 2210/21* (2013.01); *G16H 40/67* (2018.01)

(58) Field of Classification Search
USPC ......................................................... 345/503
See application file for complete search history.

(56) References Cited

U.S. PATENT DOCUMENTS

| | | |
|---|---|---|
| 8,471,845 B1 | 6/2013 | Stich |
| 8,700,877 B2 | 4/2014 | Shebanow et al. |
| 8,736,610 B2 | 5/2014 | McCombe et al. |
| 9,058,691 B1 | 6/2015 | Zimmerman |
| 9,665,970 B2 | 5/2017 | Redgrave et al. |
| 9,984,492 B2 | 5/2018 | Obert |
| 10,489,962 B1 | 11/2019 | Clark et al. |
| 10,546,393 B2 | 1/2020 | Ray et al. |
| 10,614,611 B2 | 4/2020 | Benthin et al. |
| 10,657,700 B2 | 5/2020 | Richards et al. |
| 10,672,178 B2 | 6/2020 | Zimmerman |
| 10,930,050 B2 | 2/2021 | Saleh |
| 2007/0182732 A1 | 8/2007 | Woop et al. |
| 2009/0322752 A1 | 12/2009 | Peterson et al. |
| 2011/0050698 A1 | 3/2011 | Peterson et al. |
| 2012/0133654 A1 | 5/2012 | Redgrave et al. |
| 2012/0139926 A1* | 6/2012 | Clohset ................. G06F 40/169 345/502 |
| 2013/0147803 A1 | 6/2013 | Peterson et al. |
| 2014/0340403 A1 | 11/2014 | Droske et al. |
| 2017/0221173 A1* | 8/2017 | Acharya ............... G06F 9/4887 |
| 2017/0270146 A1 | 9/2017 | Harrison et al. |
| 2018/0182058 A1* | 6/2018 | Potter ....................... G06T 1/60 |
| 2018/0293102 A1 | 10/2018 | Ray et al. |
| 2019/0156550 A1 | 5/2019 | Stanard |
| 2019/0355166 A1 | 11/2019 | Clark et al. |
| 2020/0043218 A1 | 2/2020 | Vaidyanathan et al. |
| 2020/0051290 A1 | 2/2020 | Yang et al. |
| 2020/0051310 A1 | 2/2020 | Zimmerman |
| 2020/0051314 A1 | 2/2020 | Laine et al. |
| 2020/0051315 A1 | 2/2020 | Laine et al. |
| 2020/0051317 A1 | 2/2020 | Muthler et al. |
| 2020/0105046 A1 | 4/2020 | Wald et al. |
| 2020/0193681 A1 | 6/2020 | Saleh |
| 2020/0193684 A1 | 6/2020 | Saleh et al. |
| 2021/0295463 A1 | 9/2021 | Mandal et al. |
| 2021/0295583 A1 | 9/2021 | Vaidyanathan et al. |
| 2021/0304489 A1 | 9/2021 | Saeed et al. |
| 2021/0390757 A1 | 12/2021 | Muthler et al. |

FOREIGN PATENT DOCUMENTS

| | | |
|---|---|---|
| CN | 110858410 A | 3/2020 |
| CN | 111402376 A | 7/2020 |
| EP | 3608879 A1 | 2/2020 |

OTHER PUBLICATIONS

Notice of Allowance in CN Appl. No. 202110869849.2 dated Aug. 18, 2022, 9 pages.

Office Action in European Patent Application 21187498.7 dated Aug. 30, 2022, 4 pages.

* cited by examiner

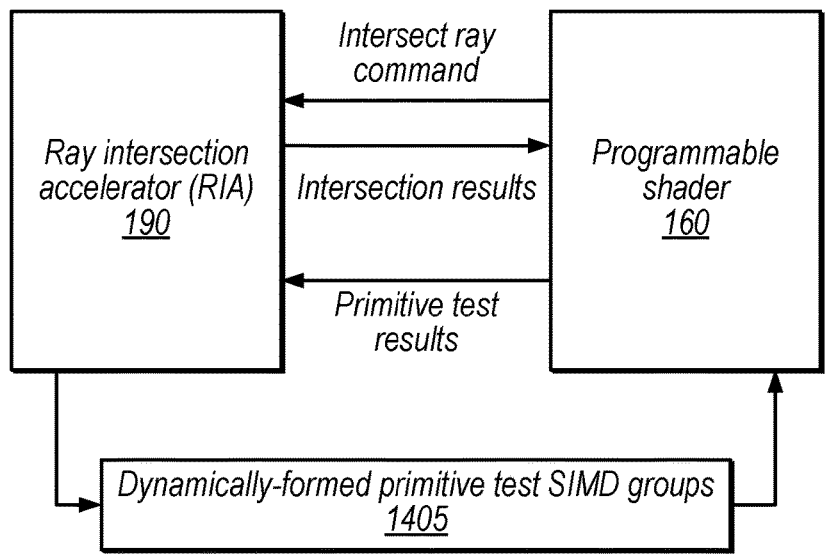

FIG. 14A

| Execute a ray intersect instruction for a first SIMD group, where the instruction indicates coordinate information for a first set of rays in a graphics scene 1410 |
|---|

↓

| Traverse, in response to the ray intersect instruction, multiple nodes in a spatially organized acceleration data structure 1420 |
|---|

↓

| Form, in response to reaching a node of the acceleration data structure that indicates one or more primitives, a second SIMD group that operates on a second set of rays that only partially overlaps with the first set of rays, where the second SIMD group executes one or more instructions to determine whether rays in the second set of rays intersect the one or more primitives 1430 |
|---|

↓

| Shade one or more primitives that are indicated as intersected based on results of execution of the second SIMD group 1440 |
|---|

FIG. 14B

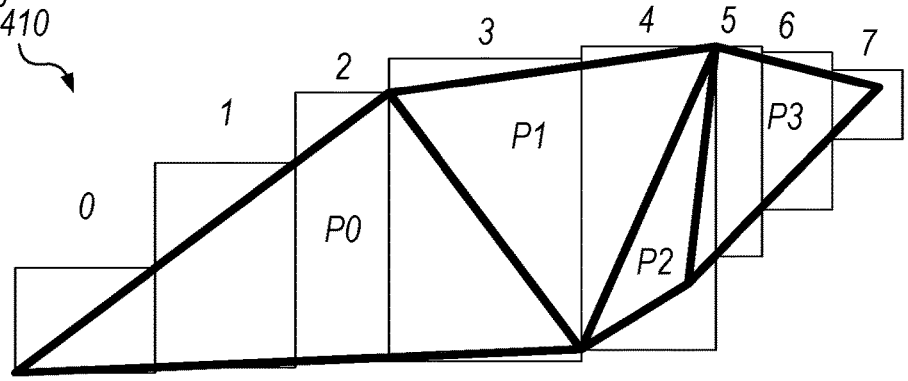
Example primitives and bounding regions 1410
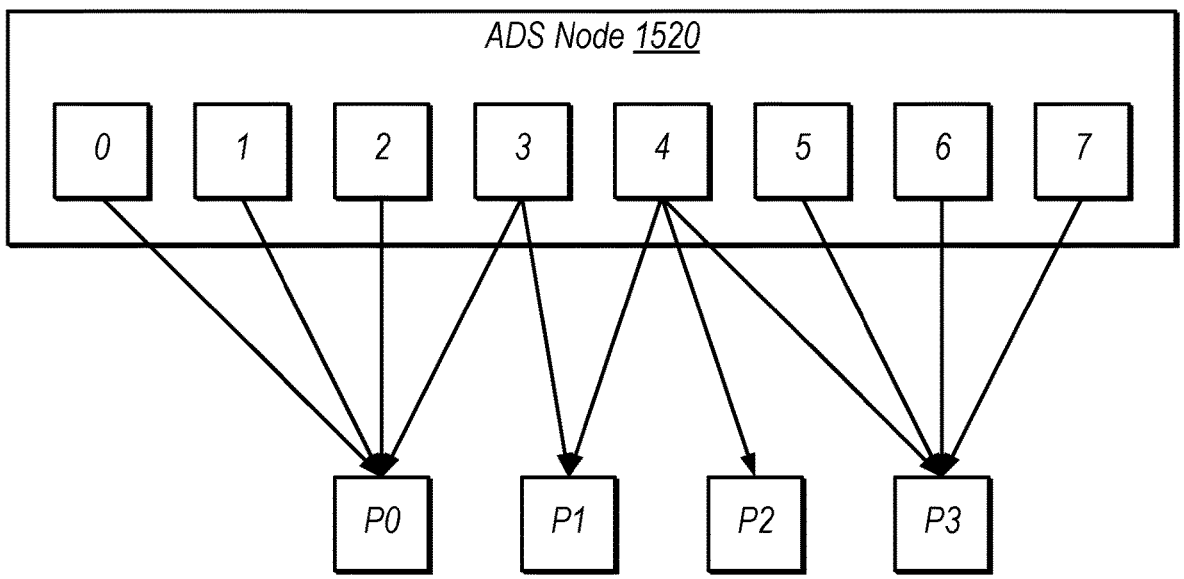
FIG. 15

GRAPHICS MEMORY SPACE FOR SHADER CORE

The present application claims priority to U.S. Provisional Application No. 63/058,868, filed Jul. 30, 2020, the disclosure of which is incorporated by reference herein in its entirety.

BACKGROUND

Technical Field

This disclosure relates generally to ray tracing in graphics processors and more particularly to circuitry configured to detect intersections between rays and graphics primitives.

Description of the Related Art

In computer graphics, ray tracing is a rendering technique for generating an image by tracing the path of light as pixels in an image plane and simulating the effects of its encounters with virtual objects. Ray tracing may allow resolution of visibility in three dimensions between any two points in the scene, which is also the source of most of its computational expense. A typical ray tracer samples paths of light through the scene in the reverse direction of light propagation, starting from the camera and propagating into the scene, rather than from the light sources (this is sometimes referred to as "backward ray tracing"). Starting from the camera has the benefit of only tracing rays which are visible to the camera. This system can model a rasterizer, in which rays simply stop at the first surface and invoke a shader (analogous to a fragment shader) to compute a color. More commonly secondary effects—in which the exchange of illumination between scene elements, such as diffuse inter-reflection and transmission—are also modelled. Shaders that evaluate surface reflective properties may invoke further intersection queries (e.g., generate new rays) to capture incoming illumination from other surfaces. This recursive process has many formulations, but is commonly referred to as path tracing.

Graphics processors that implement ray tracing typically provide more realistic scenes and lighting effects, relative to traditional rasterization systems. Ray tracing is typically computationally expensive, however. Improvements to ray tracing techniques may improve realism in graphics scenes, improve performance (e.g., allow tracing of more rays per frame, tracing in more complex scenes, or both), reduce power consumption (which may be particularly important in battery-powered devices), etc.

BRIEF DESCRIPTION OF THE DRAWINGS

FIG. 14A is block diagram illustrating an example technique for dynamically forming SIMD groups for primitive testing, according to some embodiments.

FIG. 14B is a flow diagram illustrating an example method for dynamically forming SIMD groups for primitive testing, according to some embodiments.

FIG. 15 is a diagram illustrating an example many-to-many mapping between bounding regions and primitives, according to some embodiments.

DETAILED DESCRIPTION

Figure 1A:
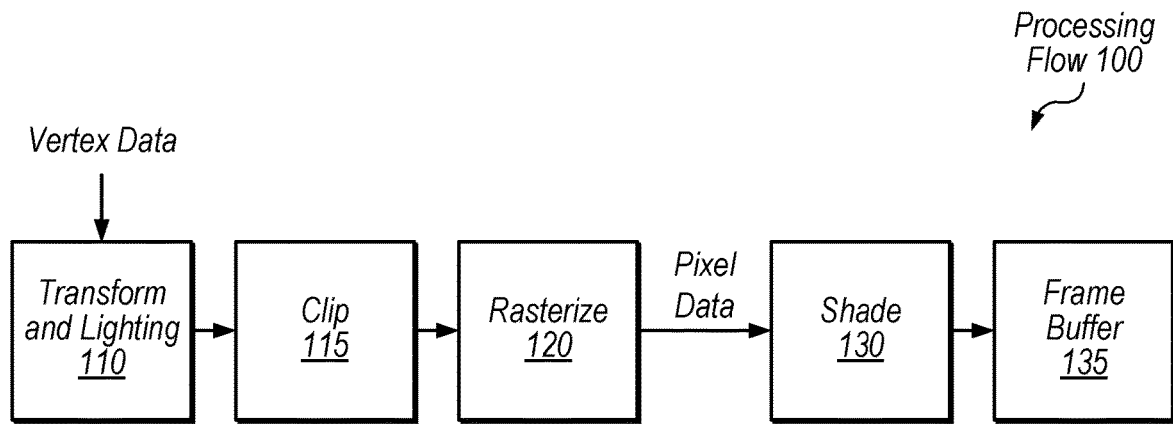
FIG. 1A is a diagram illustrating an overview of example graphics processing operations, according to some embodiments.

The present disclosure sets out various ray tracing techniques, and ray intersection techniques in particular. FIGS. 1A-2 provide an overview of graphics process and ray tracing in general. FIGS. 3A-6 provide an introduction to example embodiments of ray intersection accelerator circuitry.

Figure 7:
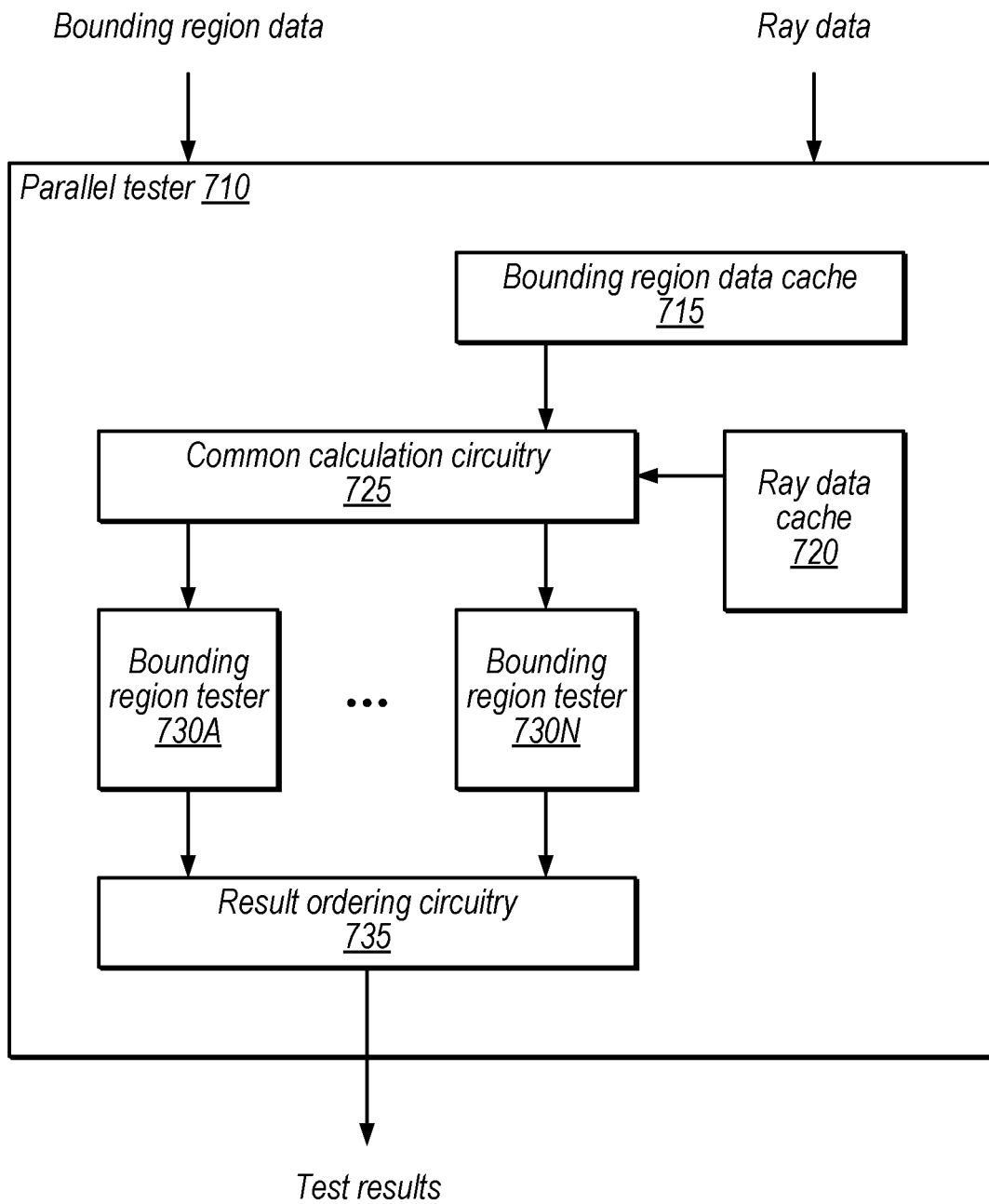
FIG. 7 is a block diagram illustrating detailed example parallel bounding region test circuitry, according to some embodiments.
Figure 8:
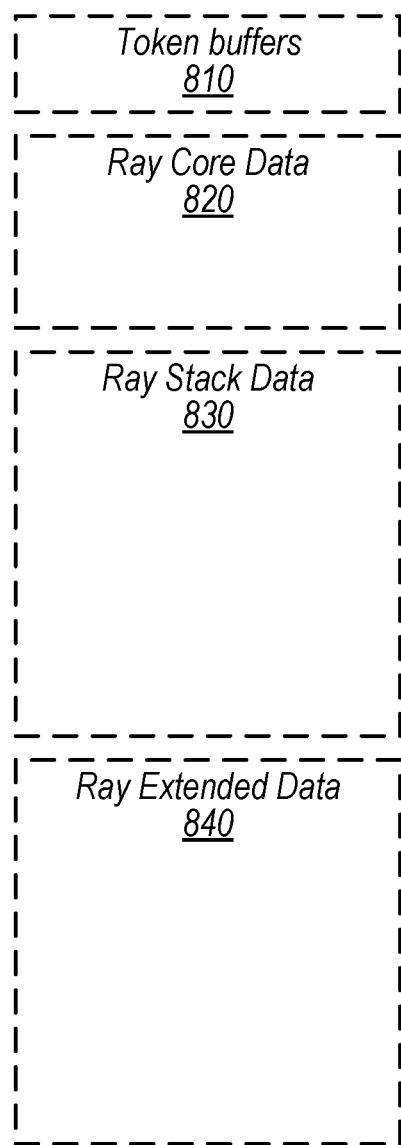
FIG. 8 is a diagram illustrating example organization of a ray shader core space (SCS) for storing ray data, according to some embodiments.
Figure 9:
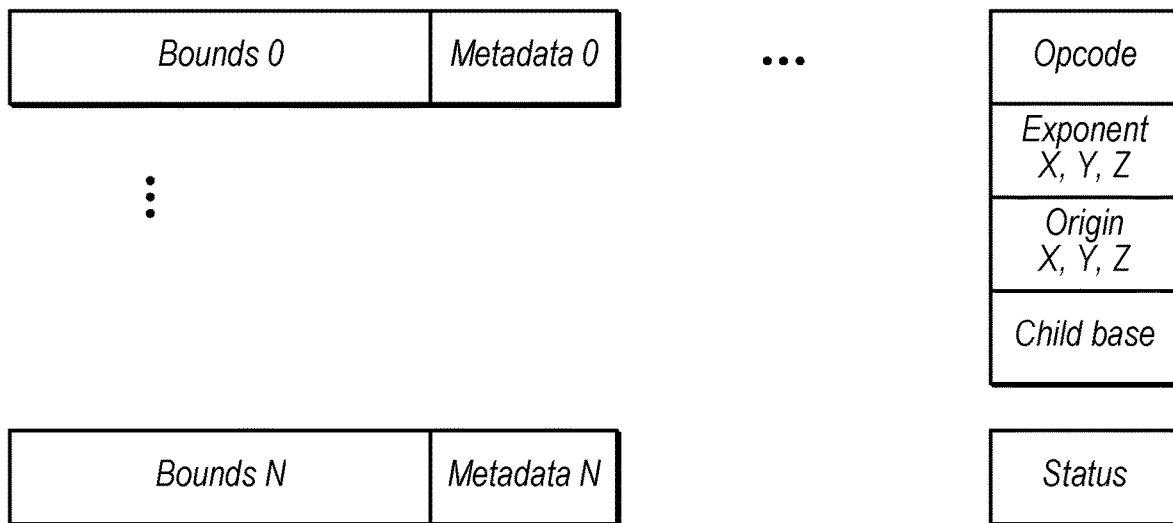
FIG. 9 is a diagram illustrating an example node data structure, according to some embodiments.
Figure 10:
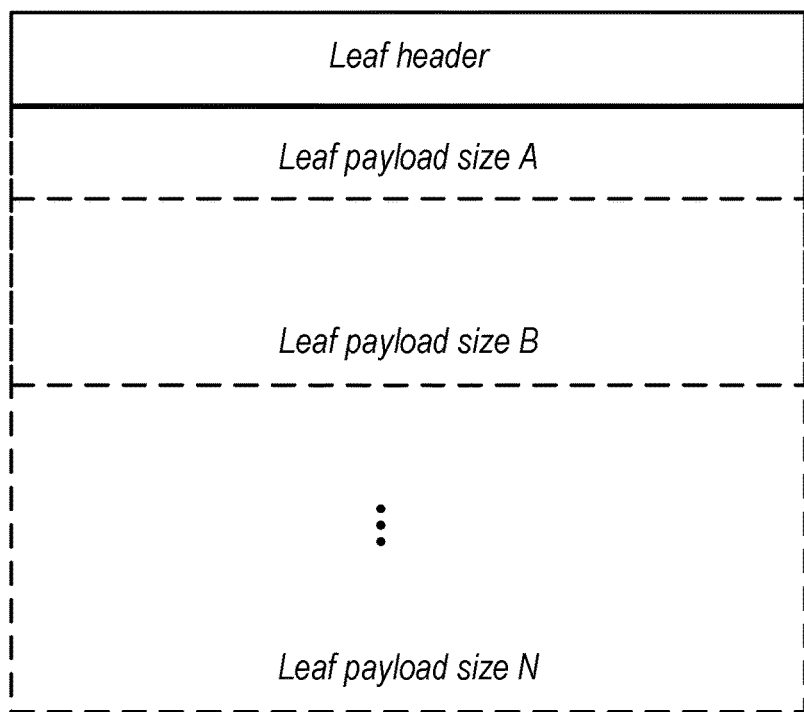
FIG. 10 is a diagram illustrating an example configurable-size leaf data structure, according to some embodiments.
Figure 11:
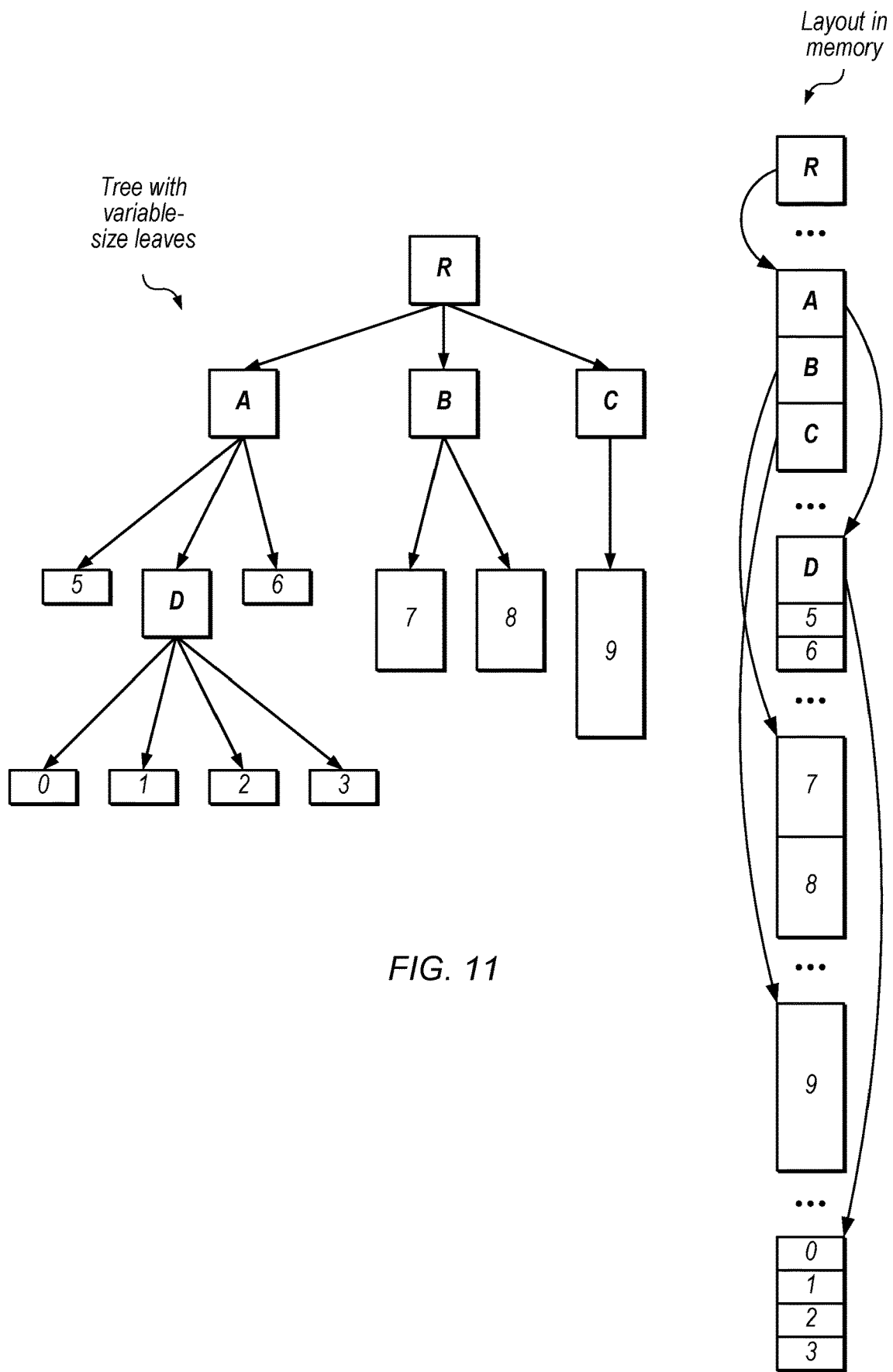
FIG. 11 is a diagram illustrating an example memory layout for an ADS tree structure with variable-sized leaf nodes, according to some embodiments.
Figure 12:
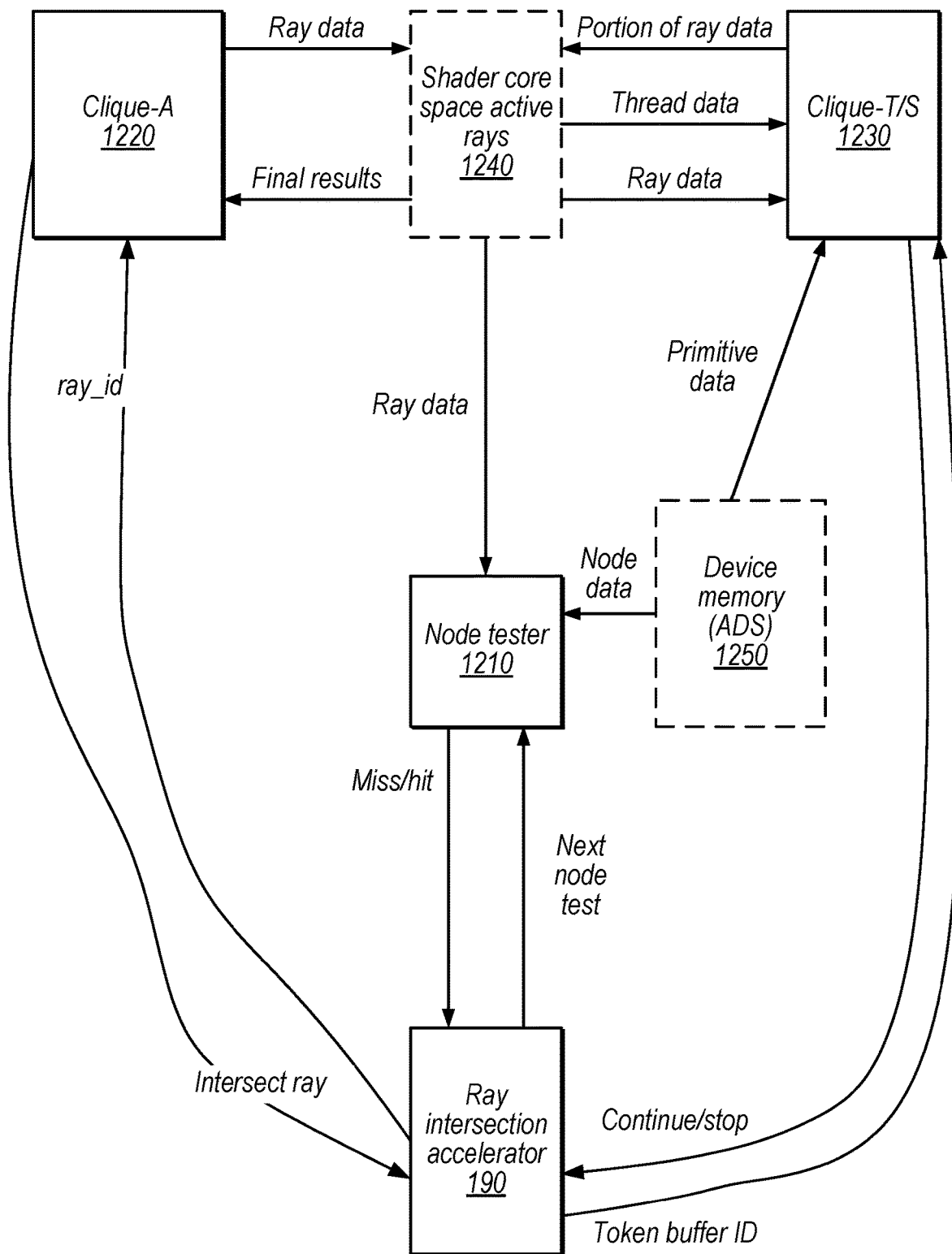
FIG. 12 is a diagram illustrating an example data flow between intersection circuitry, node test circuitry, memory regions, and SIMD groups executed by shader circuitry, according to some embodiments.
Figure 13:
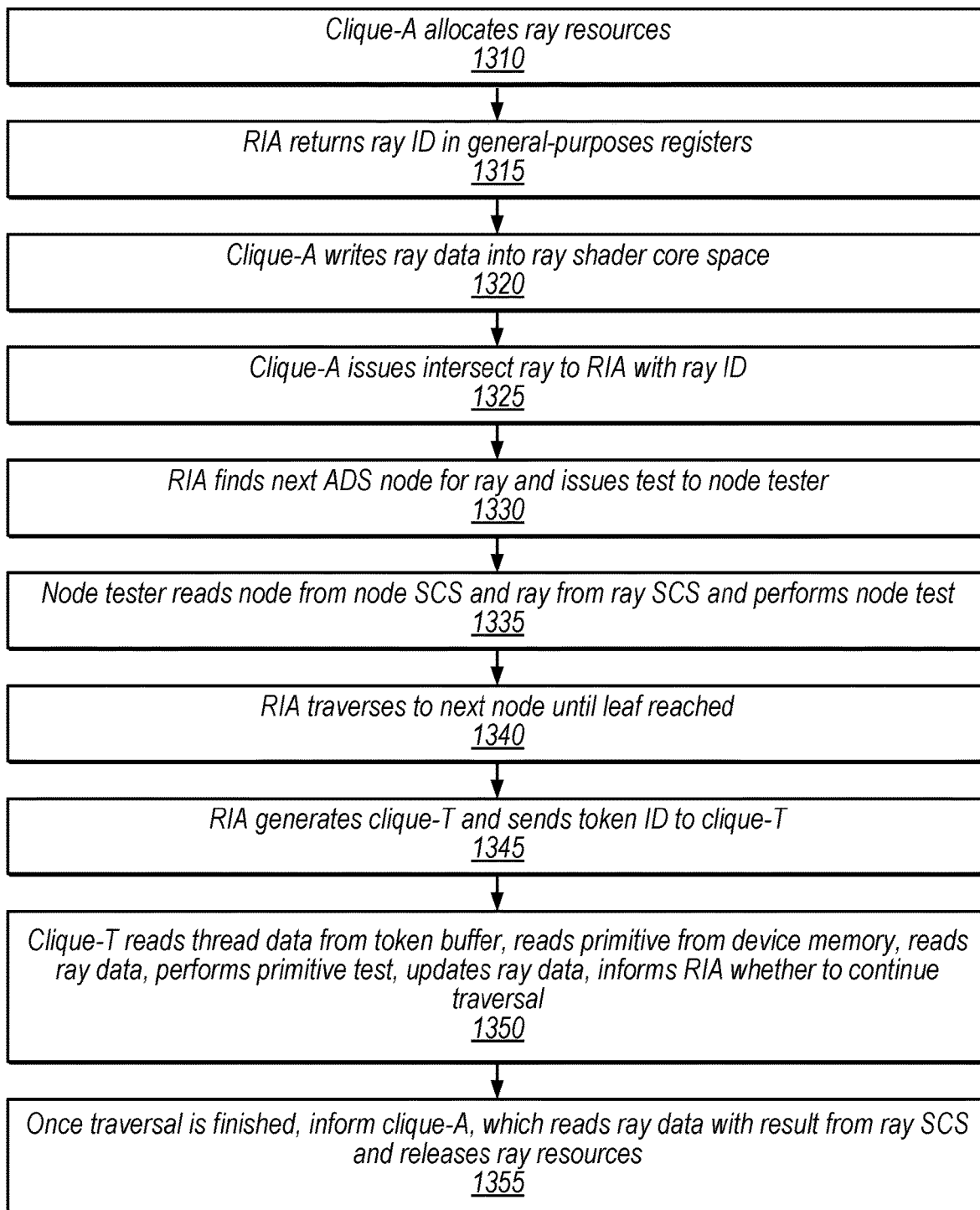
FIG. 13 is a flow diagram illustrating an example method associated with the data flow of FIG. 12, according to some embodiments.
Figure 16:
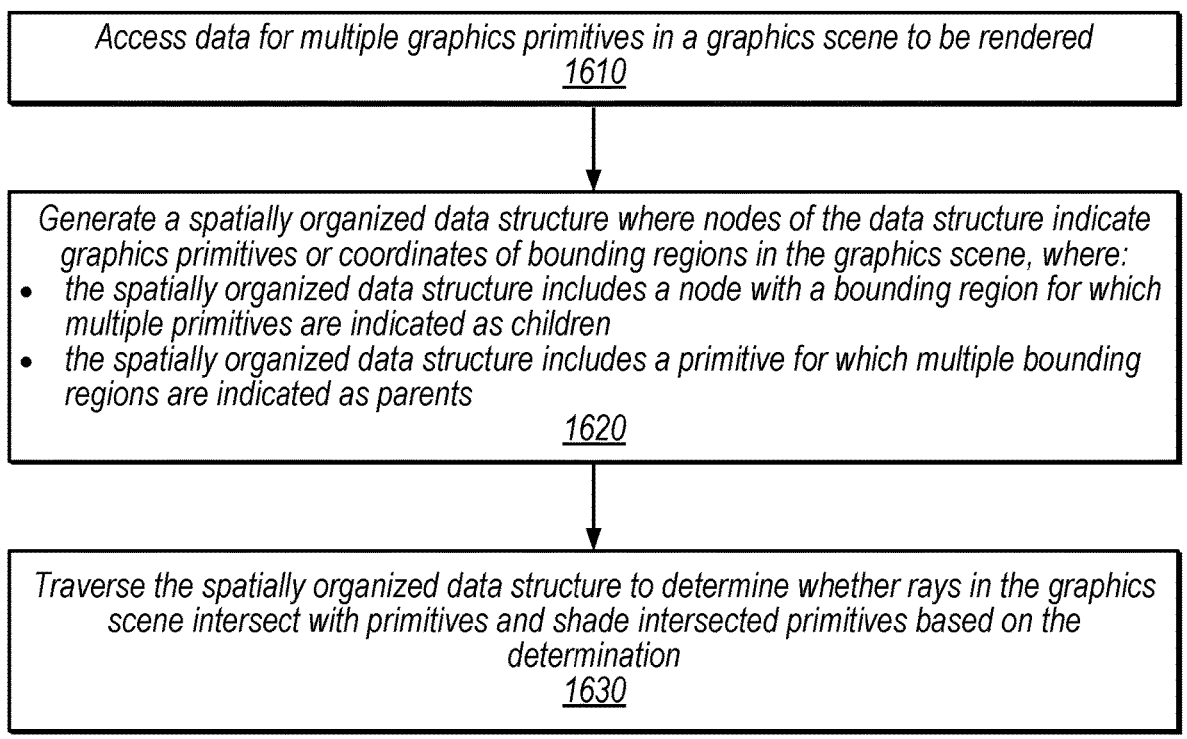
FIG. 16 is a flow diagram illustrating an example method for generating a spatially-organized data structure with a many-to-many mapping, according to some embodiments.
Figure 17:
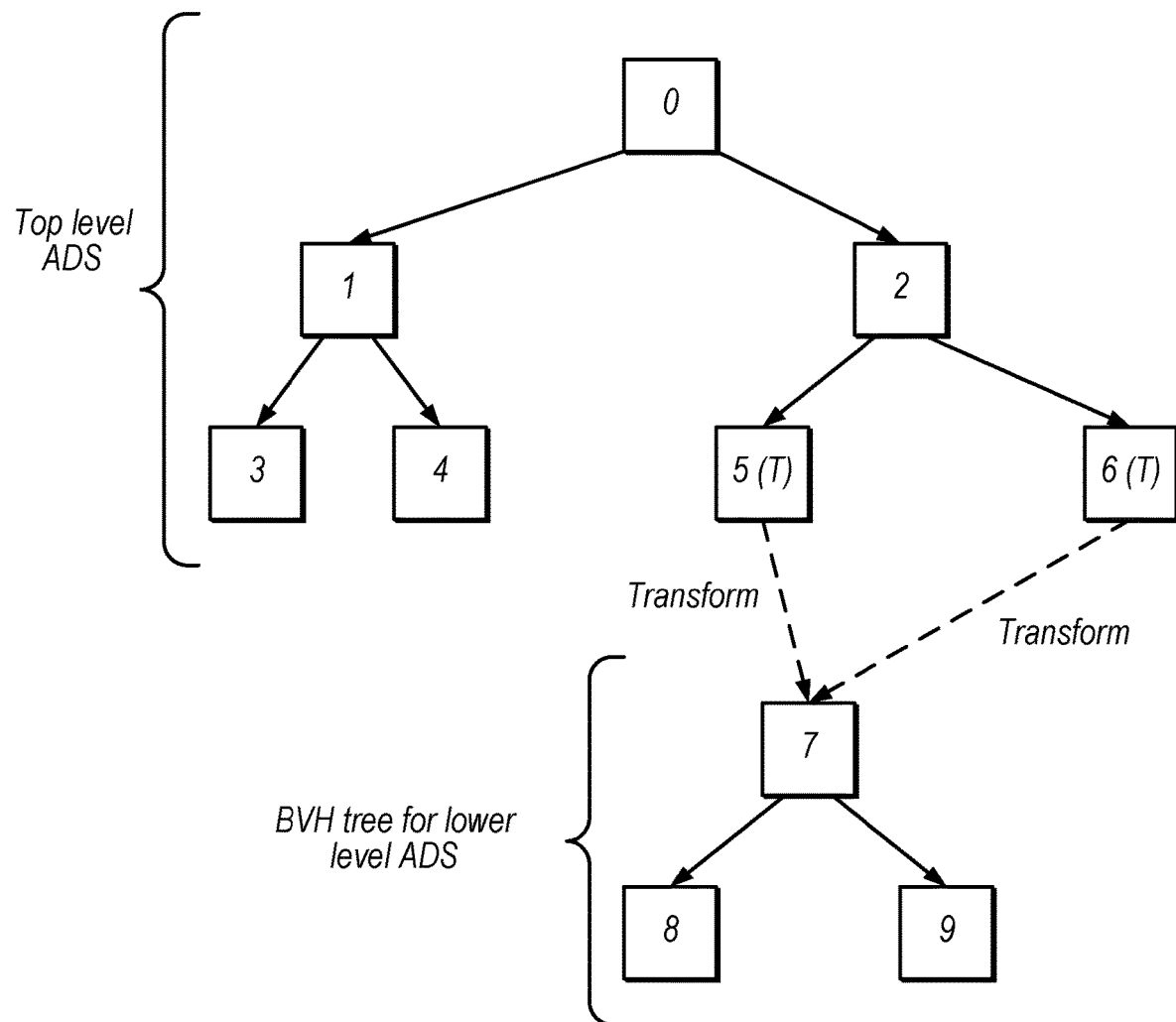
FIG. 17 is a diagram illustrating example dynamic formation of SIMD groups for ray transformation when traversing an acceleration data structure, according to some embodiments.
Figure 18:
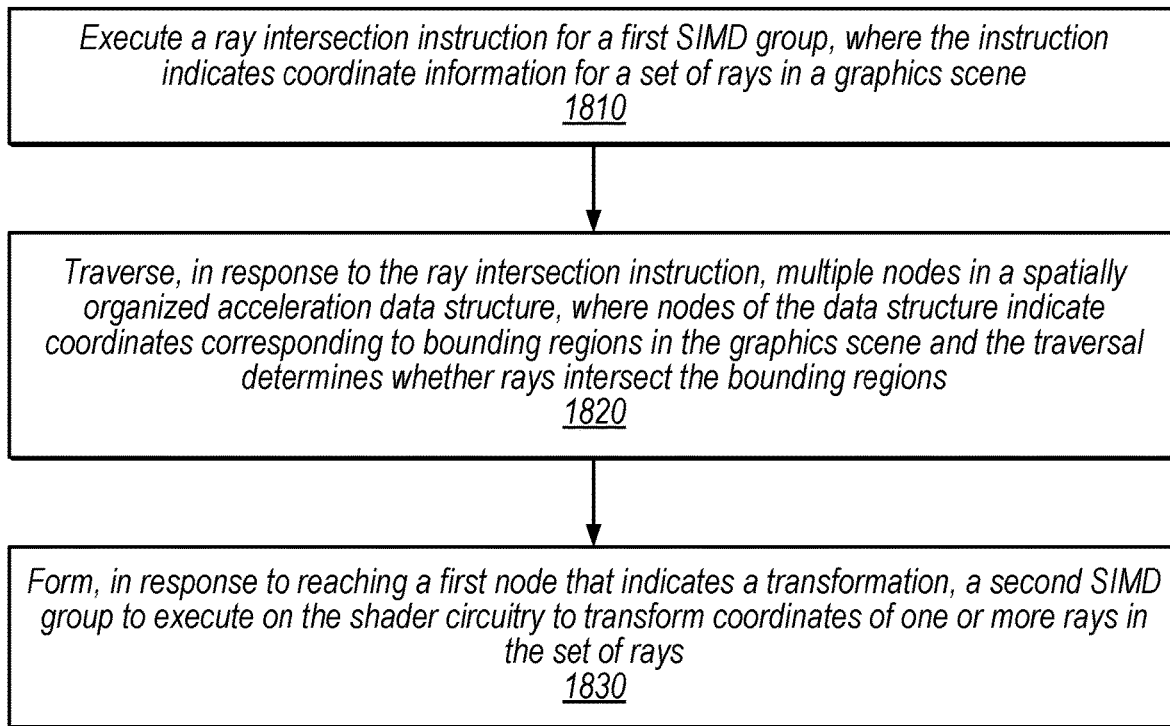
FIG. 18 is a flow diagram illustrating an example method for dynamically forming SIMD groups for ray coordinate transformation, according to some embodiments.
Figure 20:
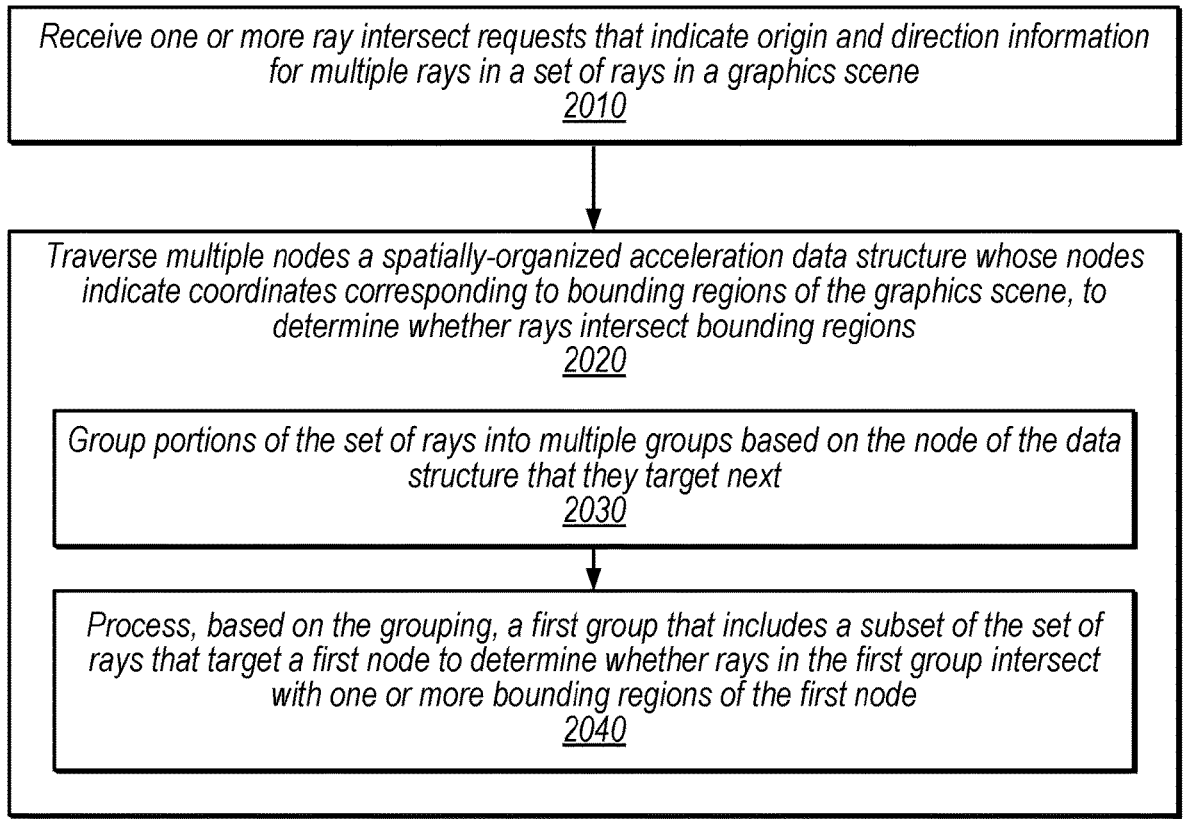
FIG. 20 is a flow diagram illustrating an example method for grouping rays during traversal of an ADS, according to some embodiments.
Figure 21:
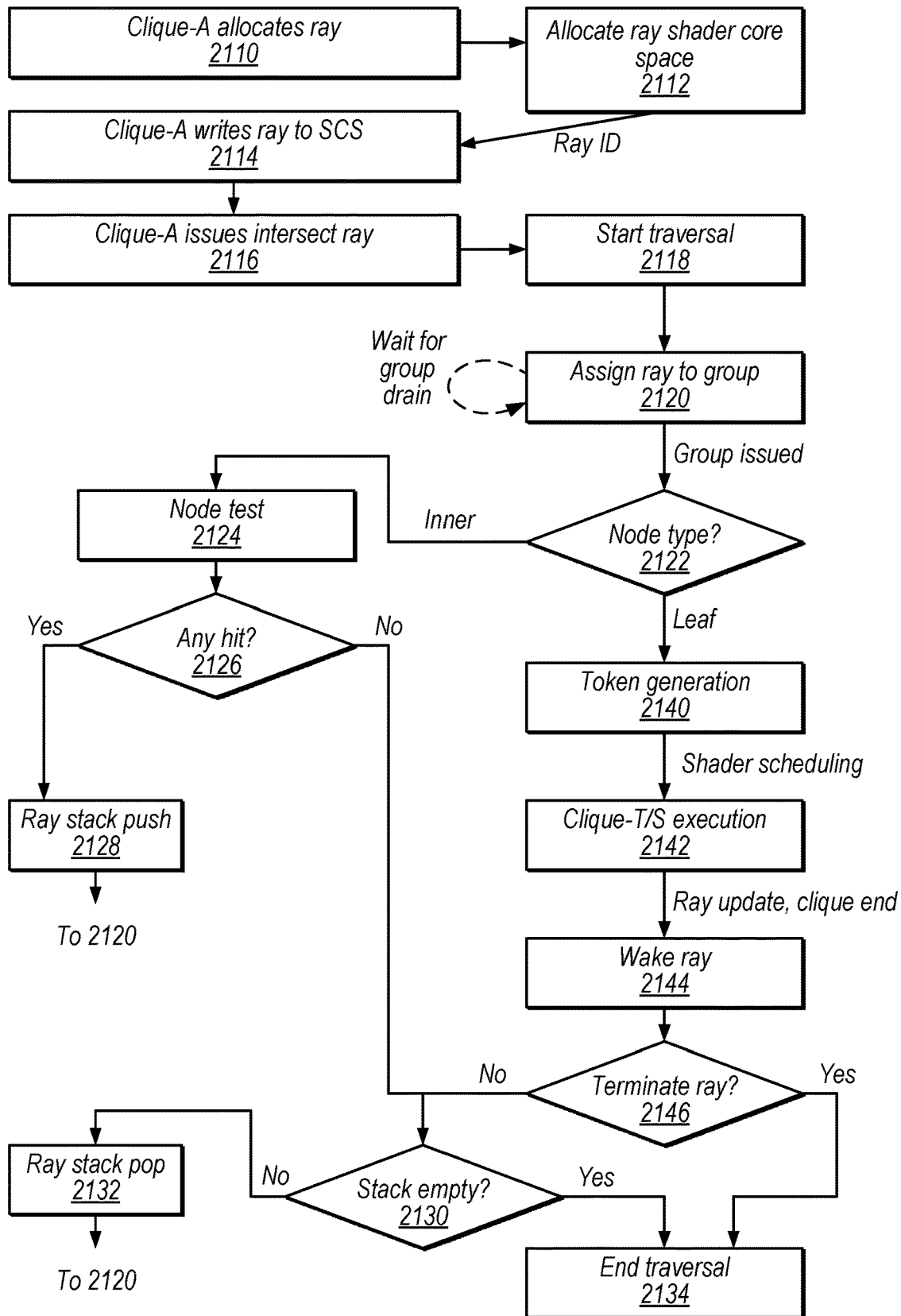
FIG. 21 is a flow diagram illustrating an example method for processing a ray, according to some embodiments.

FIGS. 7-21 provide additional details regarding embodiments of ray intersection circuitry and interactions with other graphics circuitry. In particular, FIG. 7 shows parallel node test circuitry, FIG. 8 shows a memory space used to share ray data between shaders and intersection circuitry, FIGS. 9-11 show example data structures and memory spaces, FIGS. 12-13 show example overall data flow, FIGS. 14A-14B show example techniques for dynamically forming SIMD groups for primitive testing, FIGS. 15-16 provide a many-to-many mapping between bounding regions and primitives, FIGS. 17-18 provide example techniques for dynamically forming SIMD groups during traversal (e.g., for ray transformation), FIGS. 19-20 provide example ray grouping techniques for node testing, and FIG. 21 provides an overall flowchart for ray intersect operations. FIGS. 21-25 provide details regarding the scope of a shader core memory space.

Figure 26:
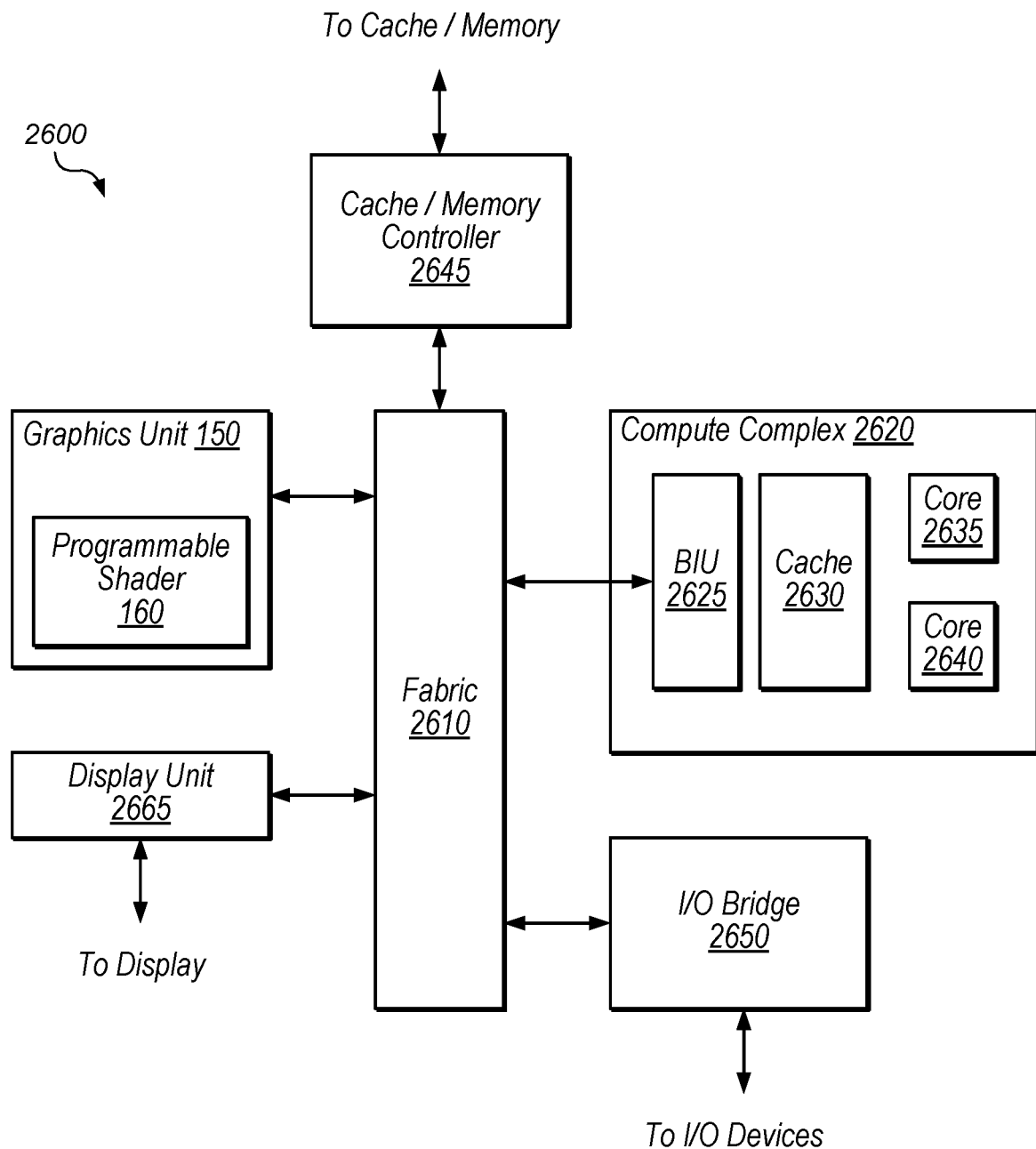
FIG. 26 is a block diagram illustrating an example computing device, according to some embodiments.
Figure 27:
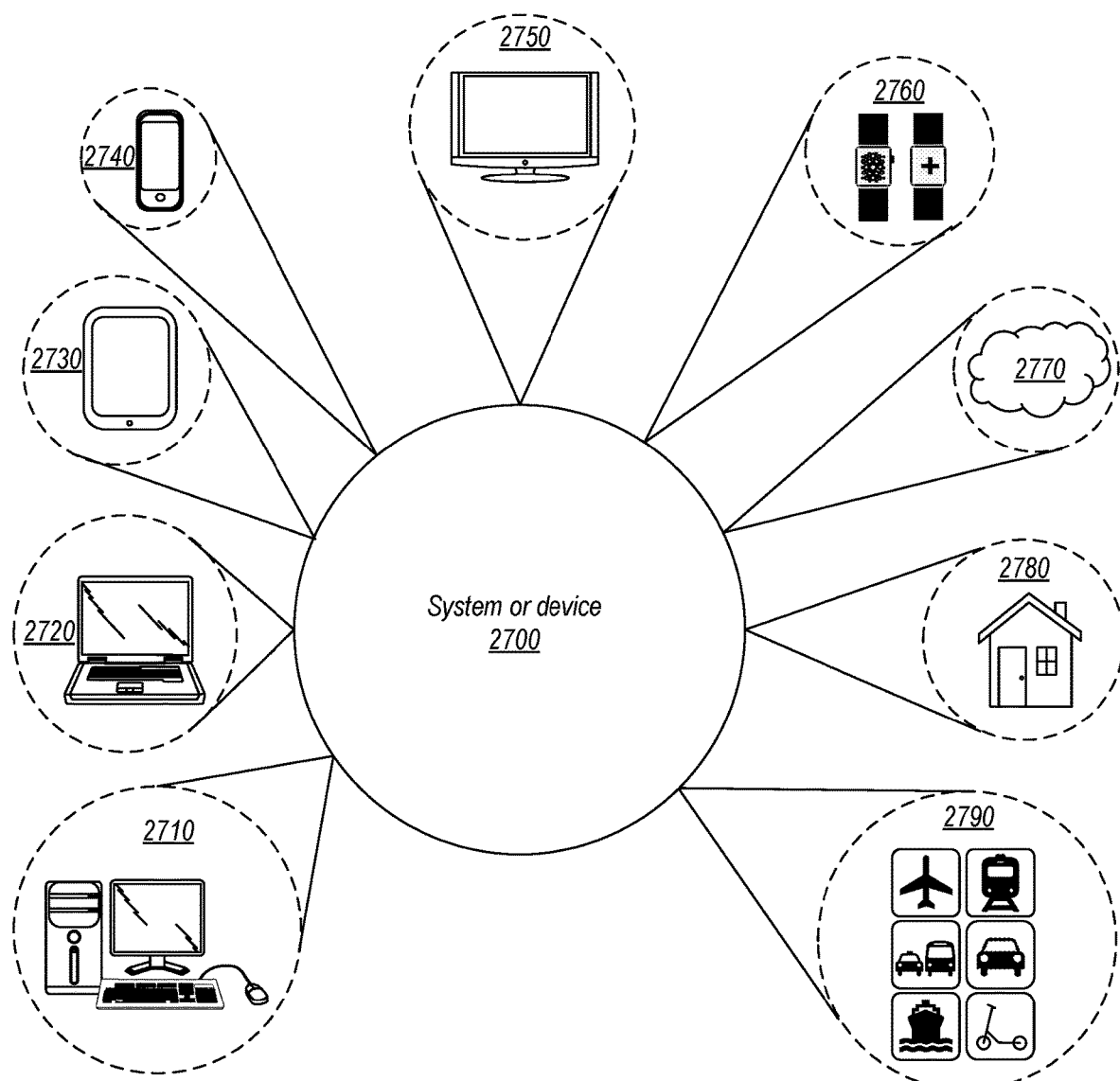
FIG. 27 is a diagram illustrating example applications of a system or device, according to some embodiments.
Figure 28:
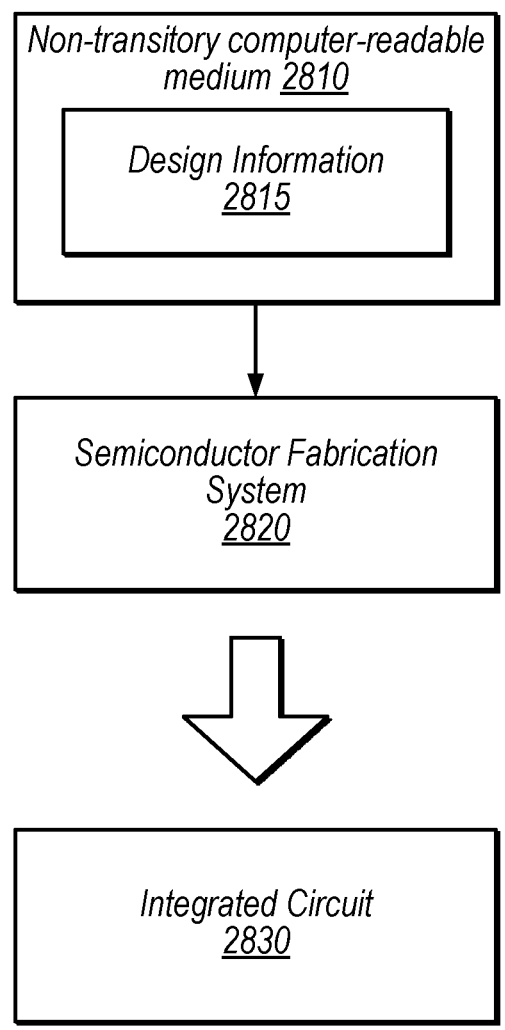
FIG. 28 is a block diagram illustrating an example computer-readable medium that stores circuit design information, according to some embodiments.

FIG. 26 shows an example computing device that may include a graphics processor, FIG. 27 shows example applications, and FIG. 28 shows an example computer-readable medium that stores circuit design information.

Graphics Processing Overview

Referring to FIG. 1A, a flow diagram illustrating an example processing flow 100 for processing graphics data is shown. In some embodiments, transform and lighting procedure 110 may involve processing lighting information for vertices received from an application based on defined light source locations, reflectance, etc., assembling the vertices into polygons (e.g., triangles), and/or transforming the polygons to the correct size and orientation based on position in a three-dimensional space. Clip procedure 115 may involve discarding polygons or vertices that fall outside of a viewable area. Rasterize procedure 120 may involve defining fragments within each polygon and assigning initial color values for each fragment, e.g., based on texture coordinates of the vertices of the polygon. Fragments may specify attributes for pixels which they overlap, but the actual pixel attributes may be determined based on combining multiple fragments (e.g., in a frame buffer) and/or ignoring one or more fragments (e.g., if they are covered by other objects). Shade procedure 130 may involve altering pixel components based on lighting, shadows, bump mapping, translucency, etc. Shaded pixels may be assembled in a frame buffer 135. Modern GPUs typically include programmable shaders that allow customization of shading and other processing procedures by application developers. Thus, in various embodiments, the example elements of FIG. 1A may be performed in various orders, performed in parallel, or omitted. Additional processing procedures may also be implemented.

Figure 1B:
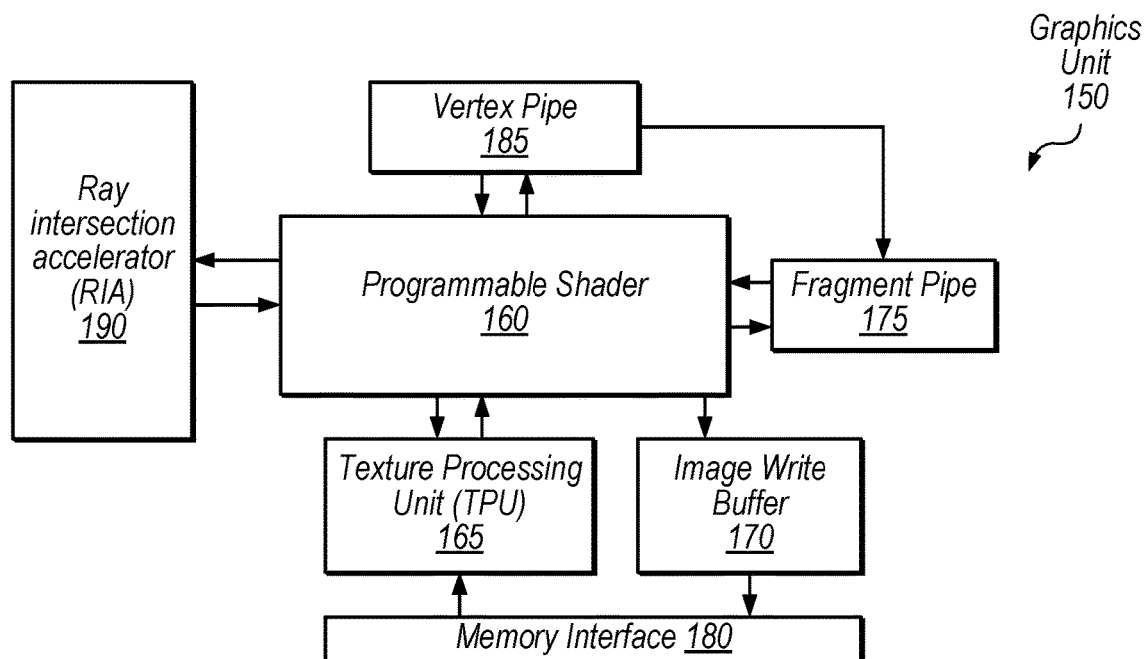
FIG. 1B is a block diagram illustrating an example graphics unit, according to some embodiments.
Figure 2:
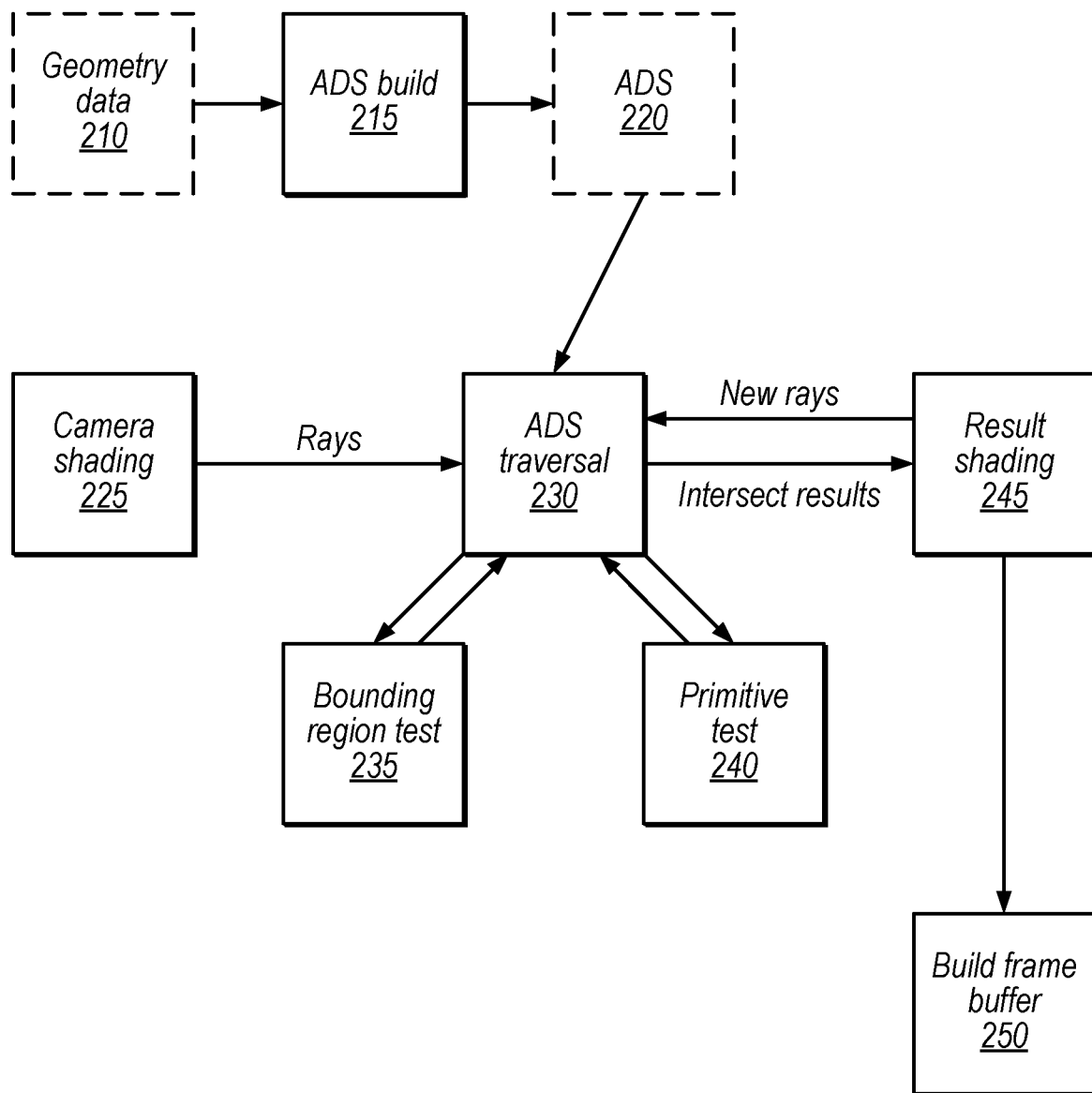
FIG. 2 is a diagram illustrating an example ray tracing procedure using an ADS, according to some embodiments.

Referring now to FIG. 1B, a simplified block diagram illustrating a graphics unit 150 is shown, according to some embodiments. In the illustrated embodiment, graphics unit 150 includes programmable shader 160, vertex pipe 185, fragment pipe 175, texture processing unit (TPU) 165, image write unit 170, and memory interface 180. In some embodiments, graphics unit 150 is configured to process both vertex and fragment data using programmable shader 160, which may be configured to process graphics data in parallel using multiple execution pipelines or instances.

Vertex pipe 185, in the illustrated embodiment, may include various fixed-function hardware configured to process vertex data. Vertex pipe 185 may be configured to communicate with programmable shader 160 in order to coordinate vertex processing. In the illustrated embodiment, vertex pipe 185 is configured to send processed data to fragment pipe 175 and/or programmable shader 160 for further processing.

Fragment pipe 175, in the illustrated embodiment, may include various fixed-function hardware configured to process pixel data. Fragment pipe 175 may be configured to communicate with programmable shader 160 in order to coordinate fragment processing. Fragment pipe 175 may be configured to perform rasterization on polygons from vertex pipe 185 and/or programmable shader 160 to generate fragment data. Vertex pipe 185 and/or fragment pipe 175 may be coupled to memory interface 180 (coupling not shown) in order to access graphics data.

Programmable shader 160, in the illustrated embodiment, is configured to receive vertex data from vertex pipe 185 and fragment data from fragment pipe 175 and/or TPU 165. Programmable shader 160 may be configured to perform vertex processing tasks on vertex data which may include various transformations and/or adjustments of vertex data. Programmable shader 160, in the illustrated embodiment, is also configured to perform fragment processing tasks on pixel data such as texturing and shading, for example. Programmable shader 160 may include multiple sets of multiple execution pipelines for processing data in parallel.

TPU 165, in the illustrated embodiment, is configured to schedule fragment processing tasks from programmable shader 160. In some embodiments, TPU 165 is configured to pre-fetch texture data and assign initial colors to fragments for further processing by programmable shader 160 (e.g., via memory interface 180). TPU 165 may be configured to provide fragment components in normalized integer formats or floating-point formats, for example. In some embodiments, TPU 165 is configured to provide fragments in groups of four (a "fragment quad") in a 2×2 format to be processed by a group of four execution pipelines in programmable shader 160.

Image write unit (IWU) 170, in some embodiments, is configured to store processed tiles of an image and may perform operations to a rendered image before it is transferred for display or to memory for storage. In some embodiments, graphics unit 150 is configured to perform tile-based deferred rendering (TBDR). In tile-based rendering, different portions of the screen space (e.g., squares or rectangles of pixels) may be processed separately. Memory interface 180 may facilitate communications with one or more of various memory hierarchies in various embodiments.

In the illustrated example, graphics unit 150 includes ray intersection accelerator (MA) 190, which may include hardware configured to perform various ray intersection operations, as described in detail below.

Ray Tracing Overview

Ray tracing techniques typically sample paths of light through the scene in the reverse direction of light propagation, starting from the camera and propagating into the scene, rather than from the light sources (this is sometimes referred to as "backward ray tracing"). A ray may be defined using an origin (O), a direction (D), and a parametric interval (T) defining the active portion of the ray. Thus, a ray may be thought of as a line segment. A graphics processor may perform various queries for a given ray. For example, a "closest hit" query may locate the nearest intersected geometry along a ray and within the parametric interval (this may be the most common type of query). An "any hit" query may locate any intersected geometry along the ray and within the parametric interval. This type of query may be used for shadow rays, for example, to determine whether a point in the scene has visibility to the light or is occluded. Once intersected geometry has been determined, that geometry may be shaded based on the intersections, and may in turn generate more rays for intersection testing, e.g., from reflective surfaces.

Ray intersection calculations are often facilitated by acceleration data structures (ADS). To efficiently implement ray intersection queries, a spatial data structure may reduce the number of ray-surface intersection tests and thereby accelerate the query process. A common class of ADS is the bounding volume hierarchy (BVH) in which surface primitives are enclosed in a hierarchy of geometric proxy volumes (e.g., boxes) that are cheaper to test for intersection. These volumes may be referred to as bounding regions. By traversing the data structure and performing proxy intersection tests along the way, the graphics processor locates a conservative set of candidate intersection primitives for a given ray. A common form of BVH uses 3D Axis-Aligned Bounding Boxes (AABB). Once constructed, an AABB BVH may be used for all ray queries, and is a viewpoint-independent structure. In some embodiments, these structures are constructed once for each distinct mesh in a scene, in the local object space or model space of that object, and rays are transformed from world-space into the local space before traversing the BVH. This may allow geometric instancing of a single mesh with many rigid transforms and material properties (analogous to instancing in rasterization). Animated geometry typically requires the data structure to be rebuilt (sometimes with a less expensive update operation known as a "refit"). For non-real-time use cases, in which millions or billions of rays are traced against a single scene in a single frame, the cost of ADS construction is fully amortized to the point of being "free." In a real-time context, however, there is typically a delicate trade-off between build costs and traversal costs, with more efficient structures typically being more costly to build.

In some embodiments discussed in detail below, intersection circuitry is configured to traverse a BVH ADS that uses 3D axis-aligned boxes for its bounding volumes. The ADS may have a maximum branching factor (e.g., 2, 4, 8, 16, etc.) and a flexible user-defined payload (e.g., the contents at the leaves of the tree) that does not presume triangle geometry.

FIG. 2 is a diagram illustrating an example ray tracing procedure using an ADS, according to some embodiments.

The ADS build element 215 receives geometry data 210 for a graphics scene and produces an ADS 220. ADS build element 215 may build the ADS from scratch or update a prior ADS, e.g., based on changes in position of an animated object. Camera shading element 225 (which may also be referred to as a source shader) produces rays originating at the viewpoint (which may be referred to as primary rays, camera rays, or eye rays). These rays are processed by ADS traversal element 230. Traversal includes operations by bounding region (e.g., box) test element 235 and primitive test element 240 and provides intersect results for result shading element 245 (which may be referred to as a hit shader). The shading may generate additional new rays for ADS traversal. The shading may produce fragment data for building a frame buffer at element 250.

In various disclosed embodiments, intersection circuitry (e.g., a ray intersection co-processor or dedicated circuitry included in a graphics processor) is configured to perform the ADS traversal 230 and bounding region testing 235. In some embodiments, the ray intersect circuitry generates work for shader processors during the traversal, e.g., for coordinate transformations or primitives tests. The shader processors may execute SIMD groups to perform various operations discussed below.

Because there are multiple types of SIMD groups discussed herein, the following labels will be used: a "clique-A" refers to a traditional SIMD group that executes a graphics program (and may execute a ray intersect instruction), a "clique-S" refers a SIMD group formed by ray intersect circuitry for coordinate transformations, and a "clique-T" refers a SIMD group formed by ray intersect circuitry for primitive testing, as discussed in detail below.

Example Ray Intersection Circuitry

Figure 3A:
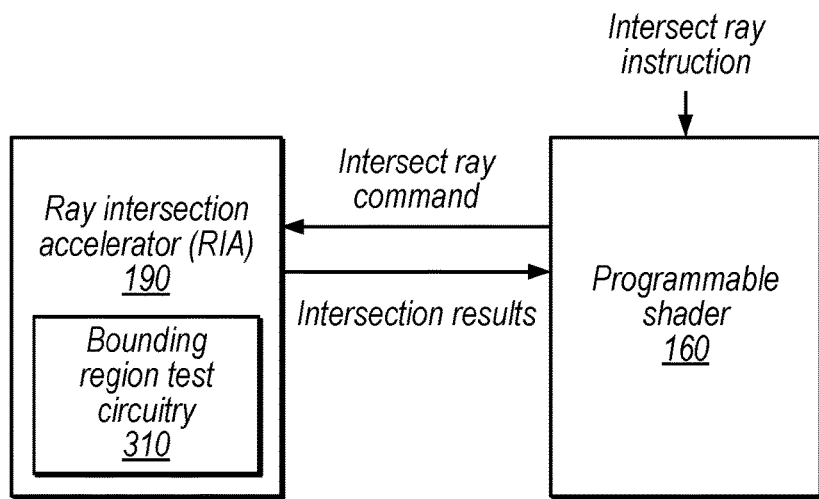
FIG. 3A is a block diagram illustrating an example graphics processor that includes shader processor circuitry and intersection circuitry, according to some embodiments.

FIG. 3A is a block diagram illustrating an example graphics processor that includes shader processor circuitry and intersection circuitry, according to some embodiments. In the illustrated embodiment, the system includes programmable shader 160 (which may execute graphics programs) and ray intersection accelerator (MA) 190 which is one example of dedicated intersection circuitry.

In the illustrated example, programmable shader 160 receives and executes an intersect ray instruction included in a graphics program. The intersect ray instruction may be a single-instruction multiple-data (SIMD) instruction, for example, and may specify multiple rays. In response, programmable shader 160 sends an intersect ray command to MA 190. The command may include a pointer to a data structure for the ray(s) being processed.

RIA 190, in the illustrated example, is configured to produce intersection results based on traversal of a spatially organized data structure (e.g., a BVH) for the scene. RIA 190 includes bounding region test circuitry, which may be configured to test a ray against multiple bounding regions (e.g., boxes) in parallel. In some embodiments, the intersection results indicate a set of primitives to be tested for intersection, e.g., RIA 190 may launch one or more SIMD groups to execute on the programmable shader 160 for primitive testing, as discussed below with reference to FIGS. 14A-14B. In other embodiments, RIA 190 may perform primitive testing and the intersection results may directly indicate intersected primitives.

The term "SIMD group" is intended to be interpreted according to its well-understood meaning, which includes a set of threads for which processing hardware processes the same instruction in parallel using different input data for the different threads. Various types of computer processors may include sets of pipelines configured to execute SIMD instructions. For example, graphics processors often include programmable shader cores that are configured to execute instructions for a set of related threads in a SIMD fashion. Other examples of names often used for a SIMD group include: a wavefront, a clique, or a warp. A SIMD group may be a part of a larger threadgroup, which may be broken up into a number of SIMD groups based on the parallel processing capabilities of a computer. In some embodiments, each thread is assigned to a hardware pipeline that fetches operands for that thread and performs the specified operations in parallel with other pipelines for the set of threads. Note that processors may have a large number of pipelines such that multiple separate SIMD groups may also execute in parallel. In some embodiments, each thread has private operand storage, e.g., in a register file. Thus, a read of a particular register from the register file may provide the version of the register for each thread in a SIMD group.

Note that various techniques disclosed as being performed using SIMD groups may be performed using single threads in other embodiments. Therefore, the SIMD examples discussed herein are not intended to limit the scope of the present disclosure. In various embodiments, SIMD techniques may improve performance relative to non-SIMD techniques, however, particularly given that graphics processors typically include substantial amounts of parallel hardware.

Figure 3B:
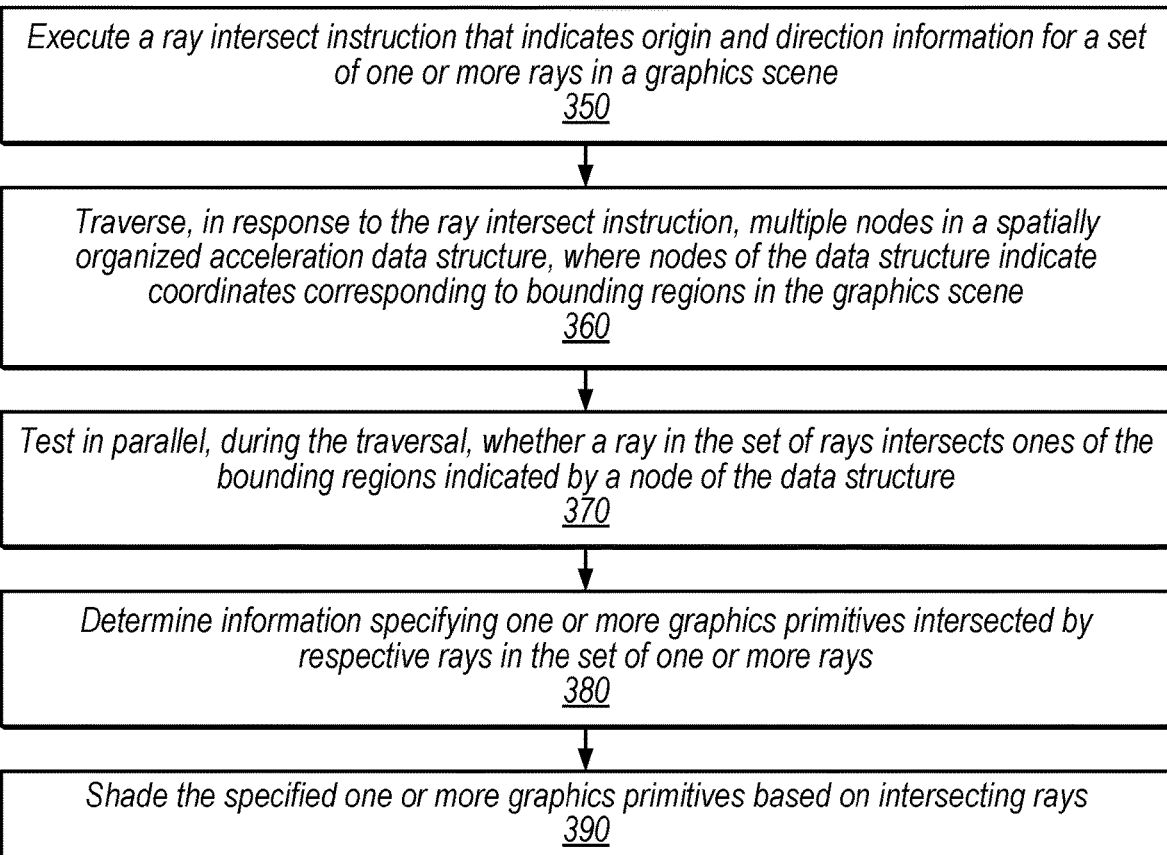
FIG. 3B is a flow diagram illustrating an example method for detecting ray intersection using ray intersection circuitry, according to some embodiments.

FIG. 3B is a flow diagram illustrating an example method for detecting ray intersection using ray intersection circuitry, according to some embodiments. The method shown in FIG. 3B may be used in conjunction with any of the computer circuitry, systems, devices, elements, or components disclosed herein, among others. In various embodiments, some of the method elements shown may be performed concurrently, in a different order than shown, or may be omitted. Additional method elements may also be performed as desired.

At 350, in the illustrated embodiment, graphics shader circuitry (e.g., programmable shader 160) executes a ray intersect instruction that indicates origin and direction information for a set of one or more rays in a graphics scene.

At 360, in the illustrated embodiment, ray intersect circuitry (e.g., RIA 190) traverses, in response to the ray intersect instruction, multiple nodes in a spatially organized acceleration data structure, where nodes of the data structure indicate coordinates corresponding to bounding regions in the graphics scene.

At 370, in the illustrated embodiment, bounding region test circuitry (e.g., circuitry 310) tests, in parallel during the traversal, whether a ray in the set of rays intersects ones of the bounding regions indicated by a node of the data structure.

At 380, in the illustrated embodiment, the device determines information specifying one or more graphics primitives intersected by respective rays in the set of one or more rays.

At 390, in the illustrated embodiment, the graphics shader circuitry shades the specified one or more graphics primitives based on intersecting rays.

The following discussion relating to various embodiments of the method of FIG. 3B provides a high-level overview of various ray intersection techniques discussed in greater detail below.

In some embodiments, the bounding region test circuitry includes multiple bounding region testers configured to determine whether a ray intersects a bounding region and configured to perform the testing for multiple bounding regions in parallel. The bounding regions test circuitry may also include common calculation circuitry configured to perform one or more operations whose outputs are shared by the bounding region testers. In some embodiments, the bounding region test circuitry further includes: a bounding region data cache, a ray data cache, and result ordering circuitry configured to order intersection results from the multiple bounding region testers based on distance to an origin of a ray being tested.

In some embodiments, the bounding region test circuitry is configured to test multiple rays in parallel against the multiple different bounding regions. In these embodiments, the bounding region test circuitry may test N rays against M bounding regions at the same time.

In some embodiments, the apparatus is configured to store ray data for the set of one or more rays in a shader memory space (which may be referred to as a ray shader core space) that is accessible to the graphics shader circuitry and the ray intersect circuitry. In some embodiments, the graphics shader circuitry is configured to generate one or more additional rays based on shading of the specified one or more graphics primitives and execute a ray intersect instruction for the one or more additional rays.

In some embodiments, the acceleration data structure is a hierarchical structure and a first node is a leaf node of an upper level acceleration data structure that has a child node in a lower level acceleration data structure. (An example of such a hierarchical structure is discussed in greater detail below with respect to FIG. 4.) The lower level acceleration data structure may correspond to a graphics model that is instantiated in the graphics scene multiple times. The ray intersect circuitry may be configured to form a SIMD group (which may be referred to as a clique-S) to transform coordinates of one or more rays that reach the first node to a model space of an instance of the graphics model.

In some embodiments, the ADS has a relatively high branching factor, e.g., such that one or more nodes of the acceleration data structure include four or more bounding regions and four or more child nodes. In some embodiments, even greater branching factors such as eight, ten, twelve, sixteen, etc. may be supported. In some embodiments, the ADS supports a many-to-many mapping between bounding regions and primitives, e.g., such that the acceleration data structure includes node(s) with at least one bounding region for which multiple primitives are indicated as children and the acceleration data structure includes at least one primitive for which multiple bounding regions are indicated as parents.

In some embodiments, the ray intersect circuitry is configured to form a SIMD group (a clique-T) to test a set of rays against a primitive corresponding to a leaf node of the data structure.

In some embodiments, the ray intersect circuitry is configured to group, using grouping circuitry, portions of the set of rays into multiple groups based on the node of the data structure that they target next, wherein the testing is based on the groups. This may improve temporal locality of accesses to node data.

Overview of Example Tree Structure and Depth-First Traversal

Figure 4:
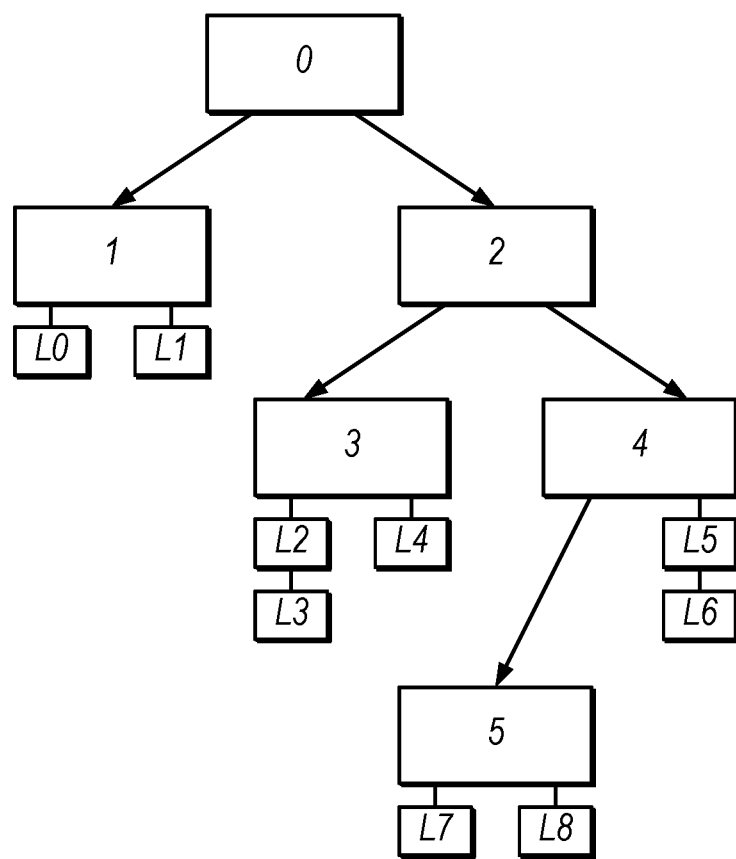
FIG. 4 is a block diagram illustrating an example ADS tree structure, according to some embodiments.

FIG. 4 is a block diagram illustrating a simplified example ADS tree structure, according to some embodiments. In the illustrated example, the tree includes nodes 0-5 and leaves L0-L8. Each node may include two or more bounding regions that each point to a child node or to one or more primitives. Conceptually, each node may store bounds for its children, but not its own bounds (which may be implied based on its parent node). In some embodiments, each leaf represents a primitive such as a triangle, which is included in a bounding region of the parent node. Detailed example data structures for nodes and leaves are discussed below with reference to FIGS. 9-10.

In the illustrated example, each node has at most two child nodes, but greater branching factors may be implemented in various embodiments. In some embodiments, a "node test" for a node includes bound tests for multiple bounding regions corresponding to child nodes. Interior nodes are nodes whose children are all nodes, such as nodes 0 and 2 in FIG. 4. Leaf nodes are nodes whose children are all leaves, such as nodes 1, 3, and 5 in FIG. 4. A mixed node has a mixture of leaf and node children, such as node 4 in FIG. 4. Tree-based ADS structures may be traversed using breadth first, depth first techniques, or a combination of the two, for example, to determine one or more primitives against which a ray should be tested for intersection.

Figure 5:
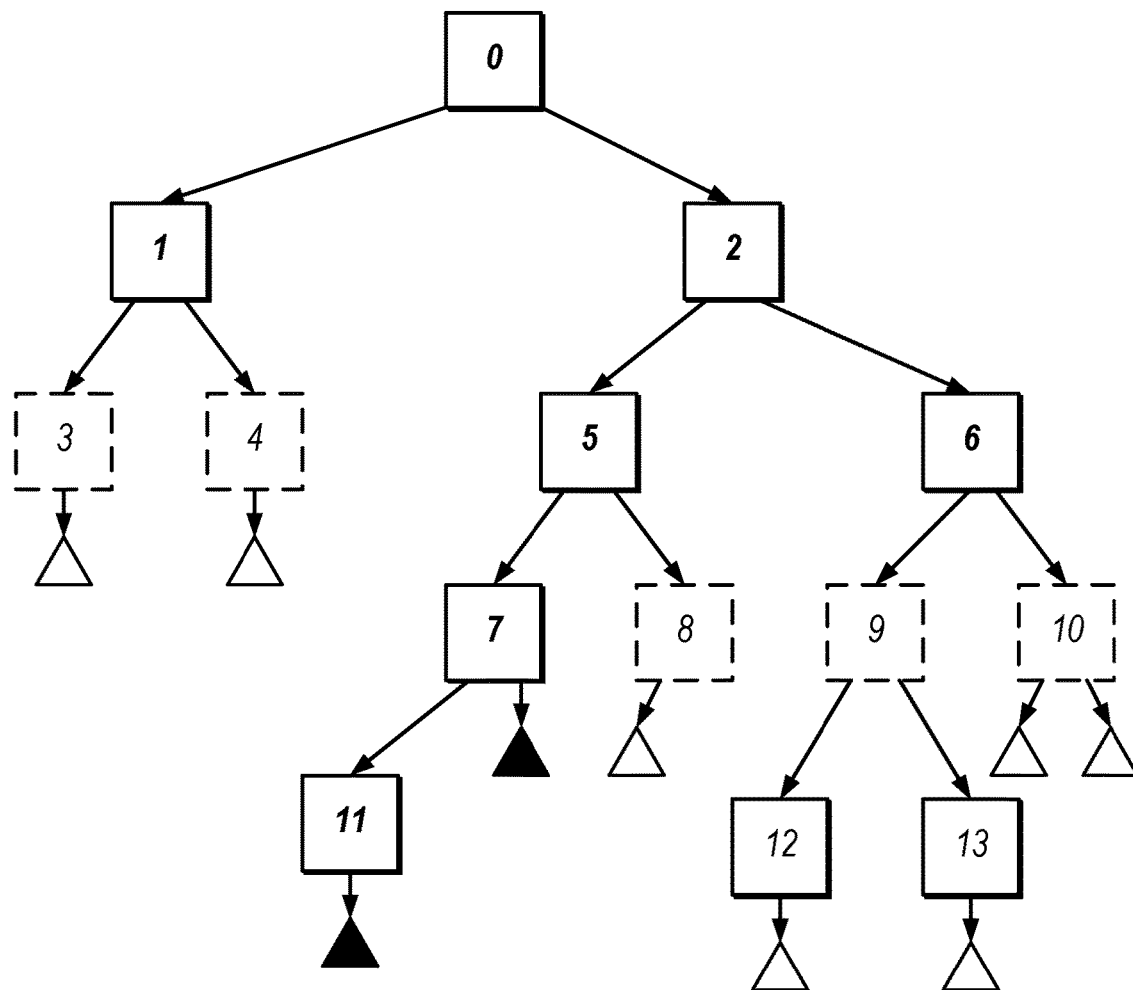
FIG. 5 is a diagram illustrating an example depth-first traversal of a BVH tree using a ray stack, according to some embodiments.

FIG. 5 is a diagram illustrating an example depth-first traversal of a BVH tree using a ray stack, according to some embodiments. In the illustrated example, the nodes shown using dashed lines were not intersected by the ray being tested and the solid triangles represent intersected primitives.

Consider the following example traversal corresponding to the situation of FIG. 5. First, a ray tests against root node 0, which corresponds to a root bounding region for the scene extents. Each time there is a hit, the children of that node are tested. In this example, both nodes 1 and 2 are hits, so the traversal continues to the children of node 2 and node 1 is pushed to the ray stack for the ray being tested. Boxes 5 and 6 are both hits and node 6 is pushed to the stack. When testing children of node 5, node 7 is a hit but node 8 is a miss, so nothing is pushed to the stack and traversal proceeds to children of node 7. Both the bounding region for node 11 its and the leaf child of node 7 are hits, so node 11 is pushed to the stack and the leaf is tested for primitive intersection.

The ray stack of FIG. 5 shows the state of the stack at this point during the example traversal, with nodes 11, 6, and 1 on the stack. At this point, a leaf has been reached and the parts of the tree that were deferred should be traversed next, which may be referred to as backtracking. The intersection circuitry pops the stack and tests the leaf of node 11 for primitive intersection. The intersection circuitry then pops the stack and tests the children of node 6, which are both misses. Nodes 12 and 13 are not reached during the traversal because their parent node 9 was not a hit. The intersection circuitry then pops node 1 and its child nodes 3 and 4 are both misses.

Note that there are multiple reasons that a parent node may be a hit, but none of its child nodes. First, due to the nature of the ADS, the parent bounding regions incorporate a larger volume than the children so it is possible that a ray that intersects the parent bounding region may not intersect the child regions. Another reason is that a ray may be shortened based on a detected intersection with a primitive. For example, after hitting the primitive child of node 7, the length of the active portion of the array may be clipped such that it does not proceed past the intersection. This may have caused the misses for nodes 3 and 4, in some circumstances. When the stack is empty and there are no further paths to pursue, the traversal may end and the intersection circuitry may return the results.

Note that various disclosed techniques may be applied to other data structure organizations (e.g., non-tree acceleration or non-BVH data structures). The disclosed data structures are included for purposes of illustration, but are not intended to limit the scope of the present disclosure. Similarly, various node structures may be implemented using one or more different node types.

Example RIA Connectivity and Region Test Circuitry

Figure 6:
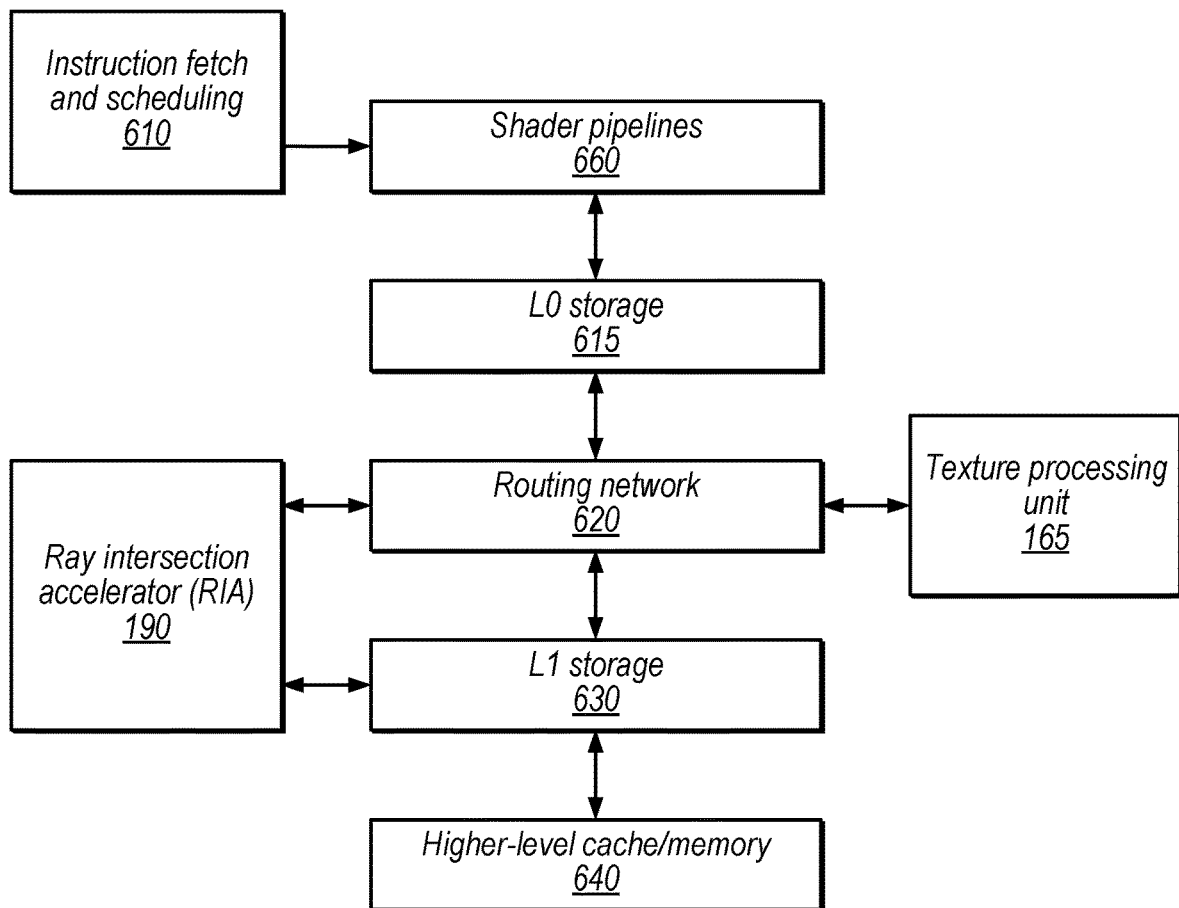
FIG. 6 is block diagram illustrating example connectivity of ray intersection circuitry to other graphics circuitry, according to some embodiments.

FIG. 6 is block diagram illustrating example connectivity of ray intersection circuitry to other graphics circuitry, according to some embodiments. In the illustrated embodiment, a graphics processor includes instruction fetch and scheduling circuitry 610, shader pipelines 660 (which may be included in programmable shader 160, for example), L0 storage circuitry 615, routing network 620, L1 storage 630, higher-level cache/memory circuitry 640, RIA 190, and texture processing unit 165.

L0 storage may be configured to store operands processed by shader pipeline 660. L1 storage 630 may be configured to store graphics data at a higher level that is also available to texture processing unit 165 and RIA 190. Routing network 620 may facilitate moving operands between lanes in the shader pipelines (e.g., between threads within a SIMD group), between different storage levels, and between L1 storage and different units such as RIA 190 and texture processing unit 165. Higher-level cache/memory circuitry 640 may include one or more L2 caches or system memory, for example. Various storage or caching elements may implement appropriate addressing or cache organization schemes. Example data structures that may be stored in one or more storage elements of FIG. 6 are discussed below with reference to FIGS. 8-11.

In some embodiments, a graphics program fetched by circuitry 610 may include a ray intersect instruction. Based on the instruction, a shader pipeline 660 may send a ray intersect command to RIA 190, which may access associated ray and geometry data via L1 storage 630. RIA 190 may also dynamically form SIMD groups for shader pipelines 660 using communications over routing network 620.

Note that the disclosed organization of circuitry in FIG. 6 is included for purposes of illustration but is not intended to limit the scope of the present disclosure. In other embodiments, any of various organization of dedicated circuitry for ray intersection and programmable shader circuitry may be implemented.

FIG. 7 is a block diagram illustrating detailed example parallel bounding region test circuitry, according to some embodiments. In the illustrated example, parallel tester circuitry 710 receives ray data and bounding region data for multiple bounding regions and outputs results indicating whether a ray intersected the bounding regions. Parallel tester 710 includes bounding region data cache 717, ray data cache 720, common calculation circuitry 725, bounding region testers 730A-703N, and result ordering circuitry 735.

In some embodiments, parallel tester 710 is a node tester configured to test up to N bounding regions, where each node in the ADS includes up to N child nodes. RIA 190 may include multiple parallel testers 710, e.g., 2, 4, 8, etc. for each programmable shader, in embodiments with M programmable shader instances. In these embodiments, each node tester may test up to M nodes per clock, per programmable shader core. In some embodiments (e.g., for example depth-first traversals discussed herein), a given ray is tested against at most one node at a time.

Bounding region data cache 715 and ray data cache 720, in some embodiments, are configured to store node and ray data respectively for the current test and for potential re-use in subsequent tests. These caches may be able to sustain a throughput corresponding to a node test per clock per tester. For tests to occur, both ray and bounding region information may be needed, so cache entries may be locked for reading until both pieces of information are available. FIG. 9, discussed in detail below, provides a detailed example encoding for bounding region data. In some embodiments, grouping rays that target the same next node may improve performance of the caches and reduce bandwidth to a higher-level cache, as discussed in detail below with reference to FIGS. 19A-19C.

Common calculation circuitry 725, in some embodiments, is configured to perform calculations that are common to all bounding regions being tested. This may include determining bounds represented using a compressed quantized format. As another example, this may include common ray calculations such as determining a reciprocal of the ray and a test point of the ray. In some embodiments, common calculations are performed at a higher floating-point precision that bounding region tests.

Bounding region testers 730, in some embodiments, are configured to test whether a ray intersects a representation of a bounding region (note that false positive may be included in embodiments with quantization, however). For box-shaped bounding regions, these testers may implement a slab test (e.g., finding the distance of each ray to the six sides of each box and comparing those values to determine whether the ray has hit in the box or not). Generally, bounding region testers 730 may include circuitry configured to perform arithmetic operations associated with the type of testing implemented and this circuitry may be pipelined. In some embodiments, bounding region testers 730 utilized lower-precision floating point arithmetic and choose rounding modes such that the calculated intersection results for the three planes facing the ray round down (towards the ray) and the intersection results for the three opposite planes facing away round up (away from the ray) to ensure that the bounding region test is conservative and does not yield false negatives.

Result ordering circuitry 735, in some embodiments, is configured to order hit results (e.g., based on their distance to the origin of the ray) and output the results for use in further traversal. Therefore, non-leaf children may be pushed onto the stack based on this ordering. In some embodiments, any leaf children may be grouped into a single stack entry. In some embodiments, the ordering may affect traversal of the ADS, e.g., child nodes corresponding to closer hits may be traversed first during a depth-first search.

In some embodiments, parallel tester circuitry 710 is configured to save the value of the parametric internal (T) parameter at which a ray intersects a bounding region (and may save the value at a higher precision than the plane tests). This value may be referred to as T-local and may be saved in stack entries and retrieved for use as the numerical ray origin for child bounding region plane tests.

In some embodiments, multiple rays may be tested in parallel against the same node, a ray may be tested in parallel against multiple nodes, or both. For example, RIA 190 may include multiple parallel testers 710 to process all or a portion of the rays in a group of rays in parallel. In some embodiments, each bounding region tester 730 may be configured to test multiple rays against a bounding region in parallel.

Example Data Structures and Overall Data Flow

FIG. 8 is a diagram illustrating example organization of a ray shader core space (SCS) for storing ray data, according to some embodiments. The ray SCS is a private memory space that may be dynamically allocated and may allow sharing of data between different threadgroups. Further, the ray SCS may allow sharing of data between different SIMD groups from the same data master and kick slot (e.g., between clique-A, clique-S, clique-T, etc.). A more detailed explanation of the concept of a data master and a graphics kick is discussed below at the end of the discussion of FIG. 8. The graphics processor may also include other memory spaces such as thread private address space, threadgroup address space, and device address space.

The SCS may be allocated at the start of a graphics kick, for example. The shader core space may advantageously allow sharing between different types of SIMD groups (e.g., clique-A types and clique-T or clique-S types), allow smaller numbers of bits for addressing ray data (relative to using addresses of a larger memory space), allow dynamic allocation of pages for data, or any combination thereof. For example, the techniques for dynamic private memory allocation discussed in U.S. patent application Ser. No. 16/804,128, filed Feb. 28, 2020 may be used to dynamically allocate pages for the ray shader core space.

In the illustrated embodiment, the shader core space includes regions for ray core data 820, ray stack data 830, ray extended data 840, and token buffers 810. In some embodiments, the SCS may also include a context switch buffer (not shown) to handle context saving. A shader may allocate space in the SCS using an explicit instruction (e.g., an allocate ray instruction) and free space by another explicit instruction (e.g., a release ray instruction after processing of the ray is complete).

Token buffers 810, in some embodiments, provide a scratch space for communication between the RIA 190 and SIMD groups launched on the shaders by the RIA 190. In some embodiments, these SIMD groups receive a ray identifier as part of their input data in order to access ray data already allocated in the SCS, e.g., prior to an intersect ray command. When forming a SIMD group (e.g., a clique-T for primitive testing or a clique-S for a transform), the RIA 190 may populate a buffer with the thread data needed by the SIMD group and the SIMD group may write back the results in the same buffer. In some embodiments, the token buffer stores pointers to information to be used for primitive testing or coordinate transformation. For example, this may include a pointer to a leaf address for intersection testing, along with a count of threads that share the same ray ID (which may be packed into the same clique-T) and corresponding thread identifiers. As another example, this may include a pointer to a ray for coordinate transformation.

Ray stack data 830, in some embodiments, contain stack entries for rays during traversal, e.g., as discussed above with reference to FIG. 5. Each ray may have a dedicated space for its stack, but the stacks for all rays may be interleaved, which may reduce footprint and may reduce the overall number of pages used for stack SCS. The maximum size of the stack SCS may be determined based one or more of: the size of the ray population, the number of levels in the ADS, and the branching factor of the ADS, for example.

Ray core data 820 may indicate the origin, direction, and active portion of each ray and may be indexed using a ray identifier. This region may also other data such as an epsilon and axis for watertight ray traversal. Ray extended data 840 may include additional data that is accessed less frequently, e.g., by software shaders, such as intersection results, ray differentials, performance counters, etc. Separating ray core data 820 and extended data 840 may improve cache utilization.

Multiple "kicks" may be executed to render a frame of graphics data. In some embodiments, a kick is a unit of work from a single context that may include multiple threads to be executed (and may potentially include other types of graphics work that is not performed by a shader). A kick may not provide any assurances regarding memory synchronization among threads (other than specified by the threads themselves), concurrency among threads, or launch order among threads. In some embodiments, a kick may be identified as dependent on the results of another kick, which may allow memory synchronization without requiring hardware memory coherency support. Typically, graphics firmware or hardware programs configuration registers for each kick before sending the work to the pipeline for processing. Often, once a kick has started, it does not access a memory hierarchy above a certain level until the kick is finished (at which point results may be written to a higher level in the hierarchy). Information for a given kick may include state information, location of shader program(s) to execute, buffer information, location of texture data, available address spaces, etc. that are needed to complete the corresponding graphics operations. Graphics firmware or hardware may schedule kicks and detect an interrupt when a kick is complete, for example. In some embodiments, portions of graphics unit 150 are configured to work on a single kick at a time. This set of resources may be referred to as a "kick slot." Thus, in some embodiments, any data that is needed for a given kick is read from memory that is shared among multiple processing elements at the beginning of the kick and results are written back to shared memory at the end of the kick. Therefore, other hardware may not see the results of the kick until completion of the kick, at which point the results are available in shared memory and can be accessed by other kicks (including kicks from other data masters). A kick may include a set of one or more rendering commands, which may include a command to draw procedural geometry, a command to set a shadow sampling method, a command to draw meshes, a command to retrieve a texture, a command to perform generation computation, etc. A kick may be executed at one of various stages during the rendering of a frame. Examples of rendering stages include, without limitation: camera rendering, light rendering, projection, texturing, fragment shading, etc. Kicks may be scheduled for compute work, vertex work, or pixel work, for example.

FIG. 9 is a diagram illustrating an example node data structure, according to some embodiments. In the illustrated example, the node data structure includes bounds 0-N for multiple bounding regions associated with children of the node, metadata for each bounding region, an opcode, exponent information, origin information, child base information, status information, and shader index information.

Bounds 0-N, in some embodiments, define the bounding regions corresponding to up to N−1 child nodes. In some embodiments, these are quantized, axis-aligned bounding boxes that are defined by their upper and lower corners (e.g., with six values per box in an X, Y, Z, coordinate space). In some embodiments, these values are represented as fixed-point offsets relative to a common origin (specified by the origin X, Y, Z fields) and scale factor (e.g., a power-of-2 scale factor specified by the exponent X, Y, Z fields). The origin values may be represented as signed floating-point values, for example. This may allow encoding of all child nodes relative to parent bounds, which may avoid progressive loss of precision as the boxes become smaller in deeper parts of the tree. The parent container—the origin and exponents—may be referred to as the quantization frame for the node.

Information indicating each bounding region may be referred to as a child and may indicate an interior child, leaf child, or invalid child. The status and contents of a given child may be determined jointly based on its corresponding metadata field and status field. For example, the status field may include a bit per child that indicates whether the child is an interior node or leaf node. As another example, the status field may separately encode the number of interior nodes and the number of leaf nodes. The metadata field may indicate whether children are invalid.

The child base field may indicate a child base address for the node, relative to the base address of the BVH tree, after which the children of the node may be stored. For leaf children, the metadata field may indicate the number of leaves that are within a given bounds and indicate an offset to the child location, relative to the child base address for the overall node, at which the number of leaves are stored. For non-leaf children, the metadata field may similarly specify an offset relative to the child base address (in some embodiments, for mixed nodes, child nodes are stored first at the offset location, followed by leaves). As discussed below with reference to FIG. 15, each bounds may reference one or more leaves and each leaf may be referenced by one or more bounds.

The opcode field may define information and performance hints about a node and its children. For example, leaf stride information may define the stride between consecutive leaves in variable-size leaf embodiments. Another field in the opcode may indicate whether the children are associated with a transform, e.g., such that a clique-S should be formed to transform rays when traversing to a child (techniques for this situation are discussed below with reference to FIGS. 17-18).

In some embodiments, bounds coordinates are quantized to six, seven, or eight bits per coordinate, for example, which results in a 36, 42, or 48-bit bounds field to represent six coordinates that define a box-shaped bounding region. In some embodiments, the quantization techniques that generate quantized coordinate values (from initial values that may be represented using greater numbers of bits) ensure that there may be false positive intersection results, but not false negatives. For example, the quantization may be performed in such a manner that quantized box representations are larger than or equal to non-quantized box representations. For example, the quantization arithmetic may be configured to round in different directions for each corner (in directions that corresponds to expanding the box if rounding is performed). This may advantageously reduce the amount of data used per node without affecting accuracy and with limited increases in testing during traversal.

FIG. 10 is a diagram illustrating an example configurable-size leaf data structure, according to some embodiments. In the illustrated embodiment, each leaf includes a header and a payload, with multiple available payload sizes A-N. As discussed above, the leaf stride for leaves of a given node may be defined by header data for that node. The header may include information needed to launch a SIMD group for intersection testing for the primitive or perform a coordinate transformation for the primitive. The payload may include varying information for different types of primitives (e.g., default triangles, alpha mapped triangles, moving triangles, etc.). Examples of payload information include, without limitation: a primitive identifier, a geometry identifier, one or more vectors, etc. In some embodiments, all child leaves of a given bounds have the same size. In other embodiments, the sizes of leaves of a given bounds may be separately encoded.

FIG. 11 is a diagram illustrating an example memory layout for an ADS tree structure with variable-sized leaf nodes, according to some embodiments. The left-hand side of FIG. 11 shows a tree with a root node R, nodes A-D, and variable-size leaf nodes 0-9. The right-hand side of FIG. 11 shows an example layout of these tree elements in memory. As shown, each node includes information indicating an offset in memory to any node children, followed by any leaf children. For example, for node A, its offset points to a location at which node D's information is stored in memory, followed by leaves 5 and 6.

In some embodiments, the disclosed encoding enables undefined regions of memory following the leaf blocks (as indicated by the ellipses in FIG. 11) which the graphics driver may use for various purposes. For example, the driver may insert debug information, extended primitive information, performance counters, etc. into these portions of the tree structure.

In some embodiments, the processor is configured to split leaf data into multiple portions. For example, a leaf may be associated with a geometric primitive for which some of the data is always accessed for an intersection test and some content is rarely needed for intersection testing (e.g., uv coordinates for a punchthrough alpha texture lookup). These different types of data may be stored in core and extended portions of a leaf data structure. In some embodiments, the extended portions are stored in undefined memory regions following the leaf blocks as discussed above.

Note that the various node, leaf, and tree data structures described herein are included for purposes of explanation but are not intended to limit the scope of the present disclosure. In other embodiments, various different structures and organizations may be implemented.

FIG. 12 is a diagram illustrating example data flow between intersection circuitry, node test circuitry, memory regions, and SIMD groups executed by shader circuitry, according to some embodiments. As shown in FIG. 12, in some embodiments a graphics processor includes ray intersection accelerator 190, node tester 1210 (e.g., a parallel tester 710 of FIG. 7), and shader circuitry (such as programmable shader circuitry 160, not explicitly shown) configured to execute different types of SIMD groups: clique-A 1220 and clique-T/clique-S 1230. Further, the graphics processor implements a shader core space 1240 and a device memory space 1250 in which the ADS is stored.

FIG. 13 is a flow diagram illustrating an example method associated with the data flow of FIG. 12, according to some embodiments. At 1310, in the illustrated embodiment, a clique-A executing on a shader allocate ray resources (e.g., by sending a request to RIA 190 in response to execution of an allocate ray instruction in the shader program executed by the clique-A). At 1315, in the illustrated embodiment, RIA 190 returns one or more ray ID's in one or more general purpose registers (note that this ray allocation may be performed for multiple rays processed by the clique-A, for example). At 1320, in the illustrated embodiment, the clique-A writes ray data for one or more allocated rays into ray shader core space based on the provided ray ID(s).

At 1325, in the illustrated embodiment, the clique-A issues an intersect ray command to RIA 190 (e.g., based on execution of a intersect ray instruction) with the ray ID (potentially along with other ray IDs). This may begin the ADS traversal process. After this point, rays from a given clique-A may end up taking different paths through the ADS and may be processed separately until all rays for the clique-A have finished their traversals.

At 1330, in the illustrated embodiment, the MA 190 finds the next ADS node for the ray and issues a test for the node to node tester 1210. If this is the first time the ray is being tested, MA 190 selects the root node. At 1335, in the illustrated embodiment, node tester 1210 reads the node data and ray data from shader core space and performs the node test. It returns miss/hit information for children of the node to MA 190.

At 1340, in the illustrated embodiment, MA 190 traverses to the next node, based on the test results, until a leaf node is reached. If the next node is an internal node, flow proceeds back to 1330. If a leaf node is reached, flow proceeds to 1345. If traversal is finished, flow proceeds to 1355.

At 1345, in the illustrated embodiment, a leaf node has been reached and MA 190 generates a clique-T and sends a token buffer ID with information for the clique-T. At 1350, in the illustrated embodiment, the clique-T reads thread data (e.g., ray ID and primitive ID) from shader core space using the token ID, reads primitive data from device memory, and reads ray data from the shader core space using the ray ID. The clique-T also performs the primitive test, updates the ray data based on the primitive test (e.g., if there is a hit), and then informs RIA 190 whether to continue traversal (e.g., ending traversal for a closest hit query when a hit is detected).

Note that operations similar to those described with reference to elements 1345 and 1350 for clique-T's may be performed for clique-S's as well. At 1340, when an S-node is reached, MA 190 may generate a clique-S, read data from device memory, read the ray data, execute on a shader to perform the transformation on the ray (parameters for which may be specified using a leaf payload, for example) and appropriately update a portion of the ray data. The clique-S may then inform the MA 190 to continue traversal.

At 1355, in the illustrated embodiment, the traversal is complete and RIA 190 informs the clique-A, which reads ray data with the intersection results from the ray shader core space and releases ray resources command (after which the ray ID may be used for another ray). The processor may decrement a fence counter, e.g., so that the clique-A can wait until all its rays have finished traversal before proceeding. The clique-A may then perform fragment shading based on the intersection results, which may in turn generate additional rays in certain situations.

Dynamically Forming SIMD Groups for Primitive Testing

FIG. 14A is block diagram illustrating an example technique for dynamically forming SIMD groups for primitive testing, according to some embodiments. In the illustrated embodiment, programmable shader 160 sends an intersect ray command to ray intersection accelerator (MA) 190. The intersect ray command may be for a clique-A SIMD group that processes multiple rays, for example. RIA 190 traverses the acceleration data structure to generate intersection results for rays (which may come from various clique-A's and may take different paths through the data structure).

In the illustrated example, RIA 190 does not actually perform primitive tests once a leaf is reached, but dynamically forms primitive test SIMD groups 1405 (e.g., for groups of rays being tested against the same primitive) to be executed by programmable shader 160. Programmable shader 160 executes the primitive test SIMD groups (clique-T's) and may provide primitive test results to MA 190 (not explicitly shown). RIA 190 may aggregate test results for a given clique-A and provide the results back to programmable shader 160 when the results are ready or RIA 190 may provide results as they are complete and the clique-T may aggregate the results (e.g., using a fence instruction).

Note that the primitive test results may also indicate to MA 190 whether or not it should continue traversal for a given ray, e.g., based on whether there is a hit and the type of intersect requested. For a closest hit query, traversal ends when there is a hit.

In some embodiments, the processor is configured to group multiple leaves that share the same shader into the same clique-T so that they can be tested together. This may advantageously reduce the average latency of primitive testing. In some embodiments, the processor designates a thread for each ray as a master thread that is responsive for performing operations that are not parallelized between multiple leaf tests (e.g., operations to determine the winner and update the ray such as finding the minimum of all distances and potentially performing tie break operations for a closest hit operation). Therefore, a clique may receive data indicating ray IDs of rays being tested by the clique, primitive addresses for primitives being tested, and information indicating "thread segments," which are the threads that operate on the same ray (e.g., count and thread ID information for the thread segments).

For example, consider the following information for three rays and ten different primitives being tested:

| Ray ID | 2 | 2 | 2 | 2 | 2 | 1 | 1 | 0 | 0 | 0 |
|---|---|---|---|---|---|---|---|---|---|---|
| Prim. | 9 | 8 | 7 | 6 | 5 | 4 | 3 | 2 | 1 | 0 |
| Count | 5 | 5 | 5 | 5 | 5 | 2 | 2 | 3 | 3 | 3 |
| TID | 4 | 3 | 2 | 1 | 0 | 1 | 0 | 2 | 1 | 0 |

In this example, ray 2 is being tested against primitives 5-9 with a count value of five threads in the thread segment for ray 2 and different thread IDs (TID) 0-4 for the five threads within this thread segment. Similarly, ray 1 is being tested against primitive 3 and 4 with two threads in the thread segment. As discussed above with reference to FIG. 8, RAI 190 may store this information in a token buffer 810 for a clique-T.

In some embodiments, a clique-T executes a SIMD-scoped reduction instruction to perform non-parallel operations involved in the transform. In these embodiments, the SIMD reduction instruction may access data from multiple threads in a SIMD group to generate an output. This may replace a loop of the master thread that iterates through the threads to find the minimum of distances among threads in the thread segment for hits, for example. Using a SIMD reduction instruction instead of a loop may advantageously improve throughput.

In these embodiments the information for the clique-T may include a segment mask (SM) that denotes boundaries between segments. In this example, a logical "1" in the segment mask indicates that this is the first thread in a new thread segment.

| Ray ID | 2 | 2 | 2 | 2 | 2 | 1 | 1 | 0 | 0 | 0 |
|---|---|---|---|---|---|---|---|---|---|---|
| Prim. | 9 | 8 | 7 | 6 | 5 | 4 | 3 | 2 | 1 | 0 |
| Count | 5 | 5 | 5 | 5 | 5 | 2 | 2 | 3 | 3 | 3 |
| TID | 4 | 3 | 2 | 1 | 0 | 1 | 0 | 2 | 1 | 0 |
| SM | 0 | 0 | 0 | 0 | 1 | 0 | 1 | 0 | 0 | 0 |

The SIMD reduction instruction may use this information to operate within each thread segment without using input data from other thread segments.

U.S. patent application Ser. No. 16/597,625, filed Oct. 9, 2019 is incorporated by reference herein in its entirety, and explains various example SIMD reduction operations and lane connection networks. These operations typically take a result register and an input register and find a result across based on different instances of the input register corresponding to different threads in a SIMD group. In some embodiments, a SIMD reduction instruction takes an additional argument that indicates the segment mask. This may allow the execution pipeline to avoid carrying reduction results across thread segments, providing a separate reduction result for each thread segment. Therefore, the shader circuitry may include control circuitry configured to restrict SIMD reduction operations within a thread segment based on the segment mask.

In some embodiments, all threads in a thread segment receive the same result from the SIMD reduction operation (e.g., indicating the primitive with the closest hit). The SIMD reduction operation may support various arithmetic operations, such as minimum, maximum, add, etc.

Therefore, in some embodiments, different threads of a clique-T operate on different rays. Further, different threads of a clique-T may operate on different primitives, for the same ray or for different rays. Further, a clique-T may execution a SIMD reduction instruction that performs an operation based on input values from multiple threads that operate on the same ray and may generate the same result for each of the multiple threads in a thread segment.

FIG. 14B is a flow diagram illustrating an example method for dynamically forming SIMD groups for primitive testing, according to some embodiments. The method shown in FIG. 14B may be used in conjunction with any of the computer circuitry, systems, devices, elements, or components disclosed herein, among others. In various embodiments, some of the method elements shown may be performed concurrently, in a different order than shown, or may be omitted. Additional method elements may also be performed as desired.

At 1410, in the illustrated embodiment, shader circuitry executes a ray intersect instruction for a first SIMD group, where the instruction indicates coordinate information for a first set of rays in a graphics scene.

At 1420, in the illustrated embodiment, ray intersect circuitry traverses, in response to the ray intersect instruction, multiple nodes in a spatially organized acceleration data structure, where the nodes include multiple nodes that indicate coordinates of bounding regions and multiple nodes that indicate primitives in the graphics scene.

At 1430, in the illustrated embodiment, the device forms, in response to reaching a node of the acceleration data structure that indicates one or more primitives, a second SIMD group that operates on a second set of rays that only partially overlaps with the first set of rays, where the second SIMD group executes one or more instructions to determine whether rays in the second set of rays intersect the one or more primitives.

In some embodiments, RIA 190 forms the second SIMD group and the shader circuitry executes it. The first SIMD group and the second SIMD group may operate on a first data structure that stores information for a first ray of the one or more rays, where the first data structure is stored in a shader memory space that is also accessible to the ray intersect circuitry. For example, the first data structure may include ray core data 920, ray extended data 840, or both. In some embodiments, the second SIMD group accesses thread data from a buffer in the shader memory space (e.g., a token buffer 810) identified by the ray intersect circuitry for the second SIMD group. The shader memory space may also include a memory region for ray stack data used by the intersect circuitry. In some embodiments, primitive coordinate data for the one or more primitives and the coordinates of the bounding regions are stored in a device memory space (e.g., as part of the ADS stored in device memory 1250).

In some embodiments, the shader circuitry pauses execution of the first SIMD group (e.g., just after the intersect ray instruction or later in the program) and resumes execution of the first SIMD group to shade the one or more primitives after receiving intersect results from the second SIMD group (and potentially from other clique-T's).

At 1440, in the illustrated embodiment, the shader circuitry shades one or more primitives that are indicated as intersected based on results of execution of the second SIMD group. The shading may be performed by continuing execution of the first SIMD group.

In various embodiments, the techniques of FIGS. 14A and 14B may advantageously provide performance and power consumption benefits of dedicated bounding region testing circuitry while using shader processors to perform more complex operations like primitive testing.

Many-to-Many Mapping Between Bounding Regions and Primitives

FIG. 15 is a diagram illustrating an example many-to-many mapping between bounding regions and primitives, according to some embodiments. The upper portion of FIG. 15, in the illustrated example, shows a two-dimensional view of four primitives and eight bounding regions while the lower portion of FIG. 15 shows four leaf nodes corresponding to the four primitives and an example ADS node with eight bounding regions.

Primitives P0-P3 are triangular primitives. Bounding regions 0-7 may be bounding boxes, for example. Although primitive vertices in bounding regions are specified in three or more dimensions in various embodiments, the simplified example of FIG. 15 is shown in two dimensions to facilitate explanation.

As shown, in some embodiments the graphics processor generates and uses acceleration data structure that support many-to-many mappings between bounding regions and primitives. For example, bounding regions 0-3 are all parents of primitive P0, so a primitive may have multiple parent bounding regions. Further, bounding region 3, for example, has multiple primitive children.

Where a traditional ADS creation technique might have created a leaf node for primitive P0 at a higher level (e.g., as a child of a node that is an ancestor of bounding regions 0-3 and has a larger bounding region), disclosed techniques may wait to create a leaf for the primitive at a lower level such that it is a child of multiple smaller bounding regions. In various embodiments, the many-to-many mapping structure, combined with a relatively high branching factor, allows bounding regions to provide a tight fit around primitives. This may reduce negative primitive test results, in various embodiments. Because node testing may be relatively less expensive in terms of processing resources than primitive testing, this reduction in primitive testing may improve performance, reduce power consumption, or both. For example, a smaller number of clique-T's may be formed for a given scene when a smaller number of negative primitive tests are issued.

FIG. 16 is a flow diagram illustrating an example method for generating a spatially-organized data structure with a many-to-many mapping, according to some embodiments. The method shown in FIG. 16 may be used in conjunction with any of the computer circuitry, systems, devices, elements, or components disclosed herein, among others. In various embodiments, some of the method elements shown may be performed concurrently, in a different order than shown, or may be omitted. Additional method elements may also be performed as desired.

At 1610, in the illustrated embodiment, a graphics processor accesses data for multiple graphics primitives in a graphics scene to be rendered.

At 1620, in the illustrated embodiment, the graphics processor generates a spatially organized data structure where nodes of the data structure indicate graphics primitives or coordinates of bounding regions in the graphics scene. In the illustrated embodiment, the spatially organized data structure includes a node with a bounding region for which multiple primitives are indicated as children. Further, the spatially organized data structure includes a primitive for which multiple bounding regions are indicated as parents.

In some embodiments, the graphics processor quantizes information that indicates a first bounding region in the spatially organized data structure to represent the first bounding region using a smaller number of bits than an original representation. This quantization may reduce overall storage requirements for the ADS. In some embodiments, the quantitation is performed such that the quantized representation indicates a region that is larger than or equal to the first bounding region in every direction, thereby preventing false negative intersection results for the first bounding region. In some embodiments, the spatially organized data structure encodes a location for a node (e.g., an offset from a root location for the ADS) at which all child nodes of the node are consecutively located. In some embodiments, the spatially organized data structure specifies primitive information in leaf nodes and bounding region information in internal nodes.

In some embodiments, the spatially organized data structure includes, for a first node that indicates one or more primitives, one or more fields that indicate: an offset at which the one or more primitives are located and a number of primitives for the first node that are located at the offset.

In some embodiments, the data structure has a relatively high branching factor. For example, the spatially organized data structure may include a node that has at least four child nodes. In some embodiments, the data structure supports variable-size leaf nodes. Therefore, a first leaf node and a second leaf node in the spatially organized data structure may have different data sizes, and respective parent nodes of the first leaf node and the second leaf node may encode the different data sizes.

At 1630, in the illustrated embodiment, the graphics processor traverses the spatially organized data structure to determine whether rays in the graphics scene intersect with primitives and shades intersected primitives based on the determination. As discussed above, the processor may form clique-Ts for primitive testing and resume execution of a clique-A for shading based on the intersection results.

Dynamically Forming SIMD Groups for Ray Coordinate Transform During Traversal

FIG. 17 is a diagram illustrating example dynamic formation of SIMD groups for ray transformation when traversing an acceleration data structure, according to some embodiments. In the illustrated example, an ADS includes ten nodes 0-9. Two nodes (nodes 5 and 6, which may be referred to as S-nodes) have bounds with the same child node (node 7, which may be the root of a lower-level ADS, as discussed in detail below). These nodes may have a field indicating that a transform should be performed when traversing to the child node. For example, the opcode field discussed above with reference to FIG. 9 may indicate that a transform is to be performed (indicated as a "(T)" value in FIG. 17) for this field for nodes 5 and 6, in the illustrated example.

The RIA 190 may form a clique-S to transform coordinates of one or more rays making the traversal (e.g., that are hits in the corresponding bounding region). Programmable shader 160 may execute one or more instructions that specify mathematical operations for the clique-S to perform the transformation. In some embodiments, the clique-S operates on ray data in shader core space 1240 so that RIA 190 can continue traversal based on the transformed ray data when the transformation is finished. At some point during traversal, the RIA 190 may transform rays back to their original coordinates for further traversal, e.g., by forming another clique-S or reverting to stored original coordinates.

The ray coordinate transformation described above may be useful in various scenarios. As one example, geometry instancing is a technique that allows rendering of multiple copies of the same model in the same scene. Consider, for example, a model of a house that may be instanced multiple times in a scene to create a row of houses on a street. For each instance, a transformation matrix may be defined to transform the model from model space to world space. Ray tracing processors may support instancing using different techniques. As one example, the system may transform the model for each instance and build an ADS which includes the world space geometry for all the instances. As another example, the system may create a single sub-portion (e.g., a tree) of the acceleration data structure in model space for the geometry that is being instanced and perform the transformation to world space during the traversal of the ADS, as shown in FIG. 17. The latter technique may provide relatively smaller ADSs, due to the lack of replication of the model being instanced in the ADS.

In some embodiments, for every instance of the model space tree (e.g., nodes 7-9 in FIG. 17, which may provide a BVH tree to be used for multiple instances of the model), a copy of the root bounding region is transformed to the world space and a hierarchy is built with the root bounding region of the model as a leaf with multiple parents in the ADS. The upper hierarchy contains all of the bounding regions of all of the instances of model space trees and may be referred to as a top level ADS. The model space BVH tree that is included once in the ADS and is being instanced may be referred to as a lower level ADS.

The system may perform a transformation when traversing from the top level ADS to a lower level ADS. Either entering rays or the bounding regions themselves may be transformed. In some embodiments, the ray is transformed, as described above, because this may be less computationally expensive. For example, for an affine transform, only the origin and direction of the ray may be transformed (and not the direction). In some embodiments, for back-tracking during traversal, the reverse transformation may be performed (e.g., using a reverse transform matrix). In other embodiments, the processor may record the original ray coordinates (e.g., origin and direction), avoiding a need to perform a reduce transform. This may reduce error due to floating-point computations, for example.

In some embodiments, an ADS may include more than two hierarchical levels, with a transformation relative to the current level each time traversal proceeds to a lower level. The processor may maintain a transformation stack that stores coordinate information prior to the transform for traversal back to the previous level. The ADS may indicate that a transformation should be performed at various granularities. As one example, a node may include a single field that indicates a transformation should be performed when traversing to any of its child nodes. As another example, a node may separately encode whether transformations should be performed when transitioning to different child nodes.

In the illustrated example of FIG. 17, a model with three meshes corresponding to nodes 7-9 respectively may have been generated. In the illustrated example, this model has been instantiated twice and there is a node per instance (nodes 5 and 6) in the top-level ADS (corresponding to nodes 0-6) marked as requiring a transform. These nodes (nodes 5 and 6) are effectively leaves of the top level hierarchy.

Although disclosed techniques utilize clique-S SIMD groups executed by shader pipelines, dedicated RIA circuitry may be configured to perform transforms for S-nodes in other embodiments.

FIG. 18 is a flow diagram illustrating an example method for dynamically forming SIMD groups for ray coordinate transformation, according to some embodiments. The method shown in FIG. 18 may be used in conjunction with any of the computer circuitry, systems, devices, elements, or components disclosed herein, among others. In various embodiments, some of the method elements shown may be performed concurrently, in a different order than shown, or may be omitted. Additional method elements may also be performed as desired.

At 1810, in the illustrated embodiment, shader circuitry (e.g., programmable shader 160) executes a ray intersection instruction for a first SIMD group, where the instruction indicates coordinate information for a set of rays in a graphics scene.

At 1820, in the illustrated embodiment, ray intersection circuitry (e.g., RIA 190) traverses, in response to the ray intersection instruction, multiple nodes in a spatially organized acceleration data structure, where nodes of the data structure indicate coordinates corresponding to bounding regions in the graphics scene and the traversal determines whether rays intersect the bounding regions.

In some embodiments, the acceleration data structure is a hierarchical structure and the first node is a leaf node of an upper level acceleration data structure that has a child node in a lower level acceleration data structure. In some embodiments, the transformation positions the one or more rays in a model space for an instance of a graphics model that is instantiated multiple times in the graphics scene. Therefore, in some embodiments, a child node (e.g., a root node for the model space) of the first node also has another parent node in the upper level acceleration data structure, wherein the other parent node indicates a different transformation when traversing to the child node, wherein the different transformation is associated with a model space for a different instance of the graphics model.

In some embodiments, the acceleration data structure is a bounding volume hierarchy.

At 1830, in the illustrated embodiment, the device forms, in response to reaching a first node that indicates a transformation, a second SIMD group (e.g., a clique-S) to execute on the shader circuitry to transform coordinates of one or more rays in the set of rays.

In some embodiments, the ray intersect circuitry stores original coordinates of the one or more rays and reverts to the original coordinates in response to traversing back through the acceleration data structure past the first node.

In some embodiments, the first SIMD group and the second SIMD group access ray data for the one or more rays in a shader memory space. The first SIMD group may include an instruction to allocate memory space for the set of rays in the shader memory space prior to executing the ray intersection instruction.

In some embodiments, the second SIMD group includes one or more rays from another SIMD group that executed a ray intersection instruction. Generally, rays from a clique-A may be split up when taking different paths from traversal such that clique-S or clique-T's may operate on rays from multiple different clique-A's.

Example Ray Grouping During Traversal

Figure 19A:
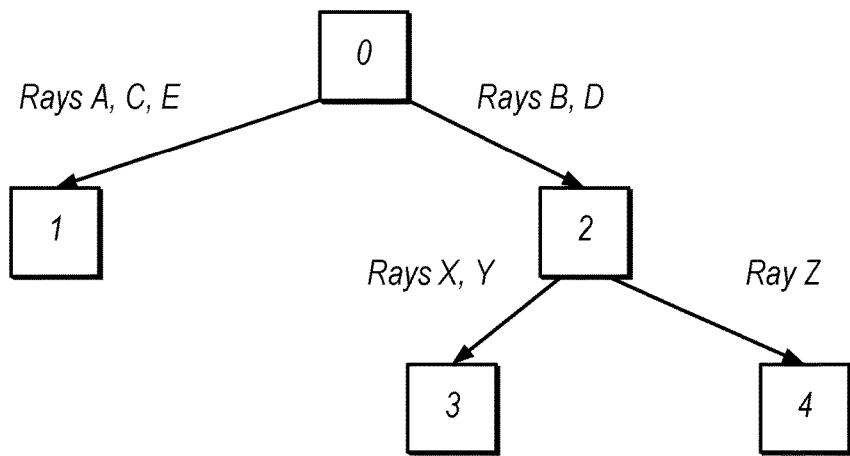
FIG. 19A is a diagram illustrating an example situation with different rays currently targeting different nodes in an ADS during their traversal, according to some embodiments.

FIG. 19A is a diagram illustrating an example situation with different rays currently targeting different nodes in an ADS during their traversal, according to some embodiments. In the illustrated example, rays A, C, and E target node 1, rays B and D target node 2, rays X and Y target node 3, and ray Z targets node 4.

In some embodiments, the graphics processor is configured to group rays to increase the number of rays testing against a node at a given time. This may also be referred to as binning or coherency gathering. Disclosed grouping techniques, discussed in detail below, may reduce bandwidth consumption, e.g., at a L1 data cache that stores node data.

In some embodiments, the graphics processor allocates each ray to a group before the ray is allowed to test. This group may be a list of rays that share the same key. For bounding region testing, the key may be the address of the node that is the next target in the traversal for the ray. As other examples, the key may be the address of a parent node or a grandparent node. For leaf testing, the key may be the leaf header virtual address. The key may also include other context information the data master and kick slot associated with the ray.

Information for each group indicates a list of rays in that group. In some embodiments, dedicated circuitry is configured to store the list of rays for each bin. In these embodiments, various numbers of entries may be used for grouping in various implementations, e.g., 64, 128, 256, or 512 groups with 4, 8, 16, 32, or 64 entries each.

Figure 19B:
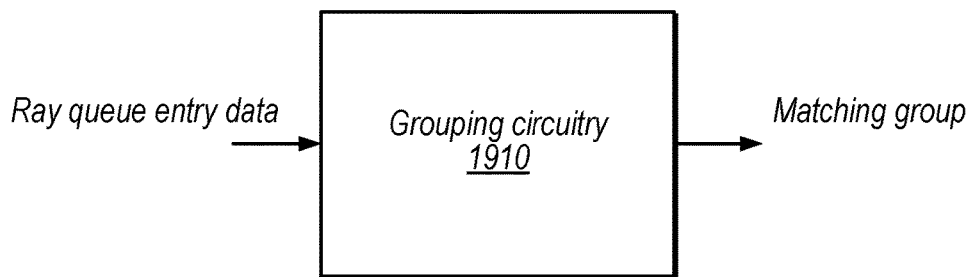
FIG. 19B is a block diagram illustrating example grouping control circuitry, according to some embodiments.

In some embodiments, each time the top of the traversal stack changes for a given ray, the RIA searches allocated groups to find a match for the corresponding key. RIA may include grouping control circuitry 1910 as shown in FIG. 19B configured to assign rays to groups. The grouping circuitry 1910 may search the groups similarly to cache lines in a set-associate cache, for example, by hashing the key to determine a set of groups and searching any allocating groups in the set of groups for a key match. In these embodiments, grouping circuitry 1910 may include content-addressable memory structures. If a match is found, RIA 190 is configured to append the ray to the matching group. If a match is not found but unallocated groups are available, RIA 190 may create a new group and assign the ray to the new group. If a match is not found and all groups are currently allocated, grouping may stall until a group becomes available.

Similar techniques may be used to group leaf nodes associated with primitives, e.g., using separate dedicated circuitry to store lists of rays that target the same leaf node (or same type of leaf, e.g., for shading coherency). In some embodiments, different numbers of groups, different numbers of entries per group, or both may be implemented for leaf nodes and internal nodes.

In some embodiments, RIA 190 also tracks the age of the oldest ray within each group. For example, the RIA 190 may maintain an age field in a control register for each group. The age field may be quantized. Each cycle, the RIA may select up to N groups with the oldest rays and issue the rays from the selected groups to issue for scheduling for node or primitive testing. In some embodiments, RIA 190 may not consider a group for scheduling until it includes a threshold number of rays. In other embodiments, various different techniques for selecting among available groups may be implemented.

In some embodiments, the matching group determined by grouping circuitry 1910 is an index into dedicated circuitry configured to store lists of rays for each allocated group. In other embodiments, the matching group may be indicated using attributes of a data structure, e.g., one or more pointers to entries in a list as discussed below with reference to FIG. 19C.

Figure 19C:
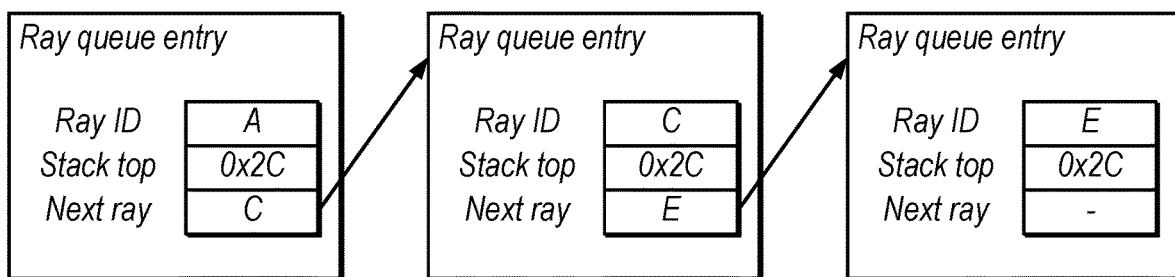
FIG. 19C is a diagram illustrating an example singly-linked list implementation for grouping rays, according to some embodiments.

FIG. 19C is a diagram illustrating an example singly-linked list implementation for grouping rays, according to some embodiments. In the illustrated embodiment, each ray queue entry indicates a ray ID (e.g., for rays A, C, and E), a stack top field that indicates the next target node (e.g., where 0x2C is a node identifier that identifies node 1 in the example of FIG. 19A), and a next ray field that indicates the location of the next ray in the list. In some embodiments, this technique may allow groups to grow indefinitely without stalling. In some embodiments, the RIA supports up to a threshold number of groups at a time. When a ray is grouped, it may be added to the end of the group list and a tail pointer maintained by the grouping circuitry 1910 may be updated. When a group is scheduled for testing, the RIA may use pointer chasing to iterate through the list and find all of the rays in the group. Although a singly-linked list is discussed for purposes of illustration, any of various other data structures may be implemented for ray grouping. Note that while a singly-linked list is shown for purposes of illustration, other data structures are contemplated.

Disclosed grouping techniques may advantageously improve temporal locality of bounding region data fetches. This may reduce cache thrashing and bandwidth to one or more data caches.

FIG. 20 is a flow diagram illustrating an example method for grouping rays during traversal of an ADS, according to some embodiments. The method shown in FIG. 20 may be used in conjunction with any of the computer circuitry, systems, devices, elements, or components disclosed herein, among others. In various embodiments, some of the method elements shown may be performed concurrently, in a different order than shown, or may be omitted. Additional method elements may also be performed as desired.

At 2010, in the illustrated embodiment, ray intersect circuitry (e.g., RIA 190) receives one or more ray intersect requests that indicate origin and direction information for multiple rays in a set of rays in a graphics scene.

At 2020, in the illustrated embodiment, the ray intersect circuitry traverses multiple nodes a spatially-organized acceleration data structure whose nodes indicate coordinates corresponding to bounding regions of the graphics scene, to determine whether rays intersect bounding regions. In the illustrated embodiment, the traversal of 2020 includes elements 2030 and 2040.

At 2030, in the illustrated embodiment, the ray intersect circuitry (e.g. using grouping circuitry 1910) groups portions of the set of rays into multiple groups based on the node of the data structure that they target next. In some embodiments, the ray intersect circuitry includes separate grouping circuitry for leaf nodes of the acceleration data structure and internal nodes of the acceleration data structure.

In some embodiments, the ray intersect circuitry assigns a ray to a new group each time the ray traverses between levels of the acceleration data structure. For example, the ray intersect circuitry may implement a traversal stack for the ray for a depth-first search of the ADS and the ray intersect circuitry may assign the ray to a new group each time the top of the traversal stack changes.

In some embodiments, to determine a group for a ray, the ray intersect circuitry uses a key that is based on the next node targeted by the ray as an input to a hash function to determine a set of groups and searches the set of groups to determine whether an allocated group in the set matches the key. The ray intersect circuitry may allocate a new group for a ray that does not match any currently-allocated group.

At 2040, in the illustrated embodiment, the ray intersect circuitry processes (e.g., using parallel tester 710), based on the grouping, a first group that includes a subset of the set of rays that target a first node to determine whether rays in the first group intersect with one or more bounding regions of the first node. In some embodiments, the processing is based on selection of one or more groups of rays during a clock cycle for scheduling for issuance to the bounding region test circuitry. In these embodiments, these groups may be drained before proceeding to process other groups, providing temporal locality for accesses to bounding region data that is cached in one or more data caches. The selection of group(s) may be based on the oldest ray in allocated groups of rays, which may provide fairness and avoid starvation.

The first group may be specified by a linked list. In some embodiments, entries in a ray queue include a field that points to a next ray in the linked list for the corresponding ray's current group. In some embodiments, the first group includes rays from multiple different SIMD groups processed by a shader processor, e.g., due to rays from a given SIMD group taking different paths through the ADS and being combined with rays from other groups. The ray intersect circuitry may include parallel test circuitry configured to test a ray against multiple bounding regions of a node in parallel. Multiple instances of the parallel test circuitry may be configured to process multiple rays in parallel.

Detailed Overall Intersection Traversal Example

FIG. 21 is a flow diagram illustrating an example method for processing a ray, according to some embodiments. The method shown in FIG. 21 may be used in conjunction with any of the computer circuitry, systems, devices, elements, or components disclosed herein, among others. In various embodiments, some of the method elements shown may be performed concurrently, in a different order than shown, or may be omitted. Additional method elements may also be performed as desired.

At 2110, in the illustrated example, a clique-A executed by a shader processor allocates a ray. At 2112 the RIA 190 allocates ray shader core space for the ray and returns a ray ID. At 2114 the clique-A writes data for the ray into the shader core space. At 2116, the clique-A issues an intersect ray instruction.

At 2118 the MA 190 begins traversal of an ADS for the ray, e.g., beginning at the BVH root node. At 2120, the MA assigns the ray to a group (e.g., using grouping circuitry) and waits for the group to drain (e.g., due to having one of the N oldest rays among active groups, or according to some other appropriate arbitration scheme among groups). Once the group is issued, RIA 190 determines the node type at 2122. If the node targeted by the group is an inner node, flow proceeds to 2124. If the node is a leaf node, flow proceeds to 2140.

At 2124, in the illustrated example, parallel tester 710 performs node testing and returns hit information for bounding regions of the node. If there are hits at 2126, flow proceeds to 2128 and the RIA 190 pushes any unpursued nodes onto the ray stack and flow proceeds back to 2120 (e.g., to traverse to the next node in the ADS). If there are no hits at 2126, flow proceeds to 2130.

At 2130, if the stack is not empty, then RIA 190 pops a node from the stack at 2120 and proceeds to 2120 (e.g., to traverse to the next node in the ADS). If the stack is empty, RIA 190 ends the traversal at 2134.

At 2140, in the illustrated example (for leaf nodes), RIA 190 generates a token ID (a pointer to a buffer in shader core space) for communication between the RIA 190 and the clique-T or clique-S to be generated for the leaf node. Each thread may retrieve its ray ID and primitive address using its thread ID in conjunction with the token ID. The shader then schedules the clique-T (for primitive testing) or clique-S (for ray coordinate transformation) and executes the clique at 2142, which updates the ray data. Once the clique has ended, RIA 190 wakes the ray at 2144 to continue traversal. If the ray is to be terminated (e.g., due to detecting an intersection for a closest-hit query), flow proceeds to 2134 and traversal ends. Otherwise (e.g., for an any-hit query), flow proceeds to 2130 and traversal may proceed if the stack is not empty.

After traversal has ended, the clique-A may read result data from the ray shader core space. RIA 190 may also release the ray, including deallocating the ray from ray shader core space.

In some embodiments, parallel tester 710 is configured to perform element 2124 of FIG. 21. In some embodiments, ray traversal control circuitry in the RIA is configured to perform elements 2112, 2118, 2120, 2122, 2126, 2144, 2146, and 2134 of FIG. 21. In some embodiments, ray stack manager circuitry is configured to perform element 2128, 2132, and 2130 of FIG. 21. In some embodiments, other graphics circuitry such as shader circuitry is configured to perform elements 2110, 2114, 2116, and 2142 of FIG. 21.

Shader Core Space

As discussed above, a shader memory space (also referred to herein as shader core space) may be accessible to multiple threadgroups executing on the same shader core, which may facilitate data sharing between the RIA 190 and different types of SIMD groups (e.g., clique-A's and clique-T's). In some embodiments, the graphics processor uses shader memory space for other operations. Speaking generally, the disclosed shader memory sharing may advantageously facilitate sharing among co-processors and shaders and sharing among threadgroups without requiring delays associated with a coherence point at a higher level memory space (such as a device or system memory space). In some embodiments, a graphics device implements the following memory spaces: thread space (a private space for a given thread, although some SIMD permutation instructions may allow limited access to data for other threads in a SIMD group), a threadgroup space (a private space for a given threadgroup), a shader memory space (accessible to multiple threadgroups executed on the same shader core and potentially to one or more co-processors for the shader core, but not to threadgroups executed by other shader cores), and a device space accessible to multiple shader cores and potentially other circuitry on the computing device (e.g., a CPU).

Using the shader memory space instead of device memory for certain types of data may advantageously provide lower latencies for that data, allow more higher-bandwidth implementations, reduce resource costs for coherency, or any combination thereof.

Figure 22A:
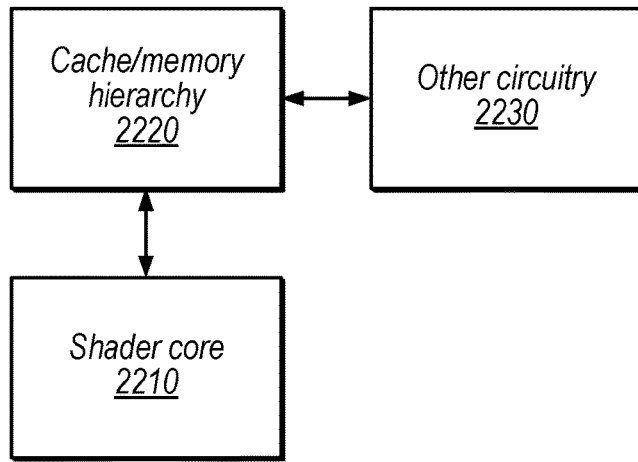
FIG. 22A is a block diagram illustrating an example cache-memory hierarchy accessible to a shader core, according to some embodiments.

FIG. 22A is a block diagram illustrating an example cache-memory hierarchy accessible to a shader core, according to some embodiments. In the illustrated embodiment, shader core 2210 and other circuitry 2230 have access to all or a portion of cache/memory hierarchy 2220. Hierarchy 2220 may include low-level circuitry like a register file, various caches (e.g., L0 (which may be closely associated with one or more ALUs, L1, L2, etc. caches for instructions and/or data) and memory circuits (e.g., random access memory, disc-based drives, solid state storage, etc.). Coherency for different memory spaces may be enforced at different levels of the hierarchy. In some embodiments, the device implements a unified memory architecture in which all storage is backed by the memory hierarchy.

Other circuitry 2230 may include other shader cores, other graphics units, other processors such as CPUs, other circuitry of a system-on-a-chip (SoC), etc. Note that circuitry 2230 and shader core 2210 may implement a portion of the hierarchy 2220 internally, in some embodiments, e.g., with private low-level caches.

Shader core 2210, in some embodiments, is one of multiple shader cores included in a graphics processor. Shader core 2210 may include one or more L1 caches that are not shared with other shader cores. Shader core 2210 may include a number of arithmetic logic units (ALUs) configured to execute instructions for SIMD groups in parallel. Shader core 2210 may be the smallest scaling unit of a GPU, e.g., the smallest unit capable of executing its own shader program. A GPU may include as few as a single shader core or as many shader cores as appropriate in larger-scale applications. For compute work, shader core 2210 may receive compute workgroups and assign workitems from the workgroups to internal processing pipelines.

Figure 22B:
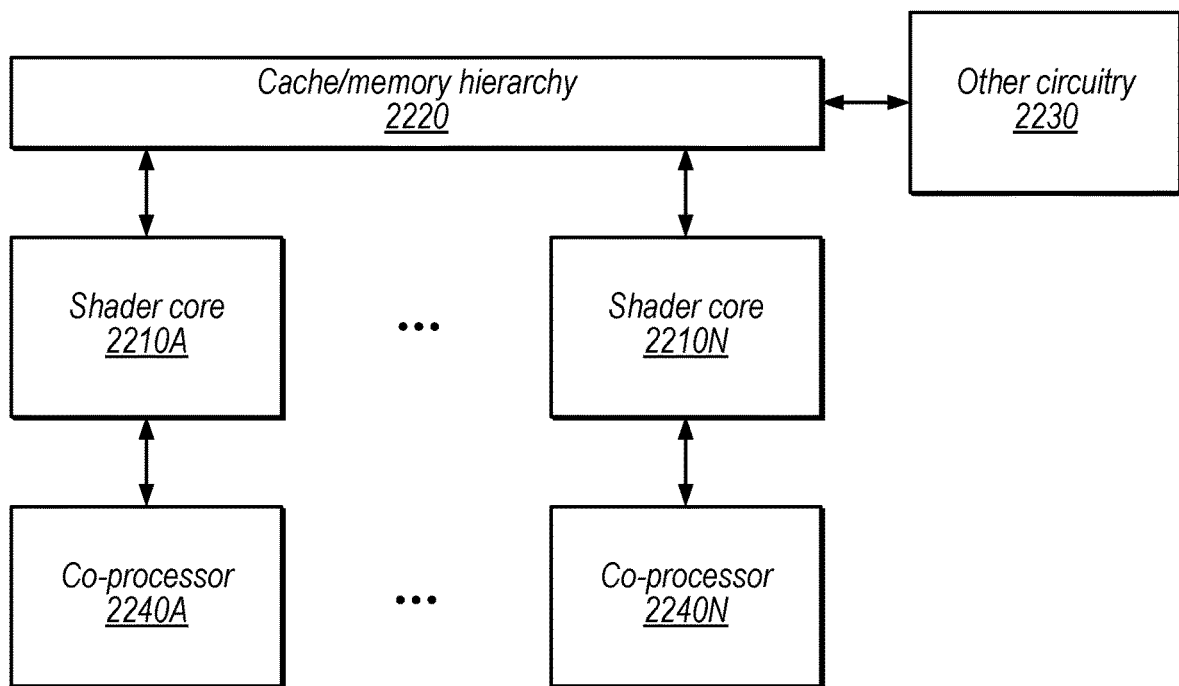
FIG. 22B is a block diagram that shows an example cache-memory hierarchy accessible to multiple shader cores and their co-processors, according to some embodiments.

FIG. 22B is a block diagram that shows an example cache-memory hierarchy accessible to multiple shader cores and their co-processors, according to some embodiments. In the illustrated example, multiple shader cores 2210A-2210N and their co-processors 2240A-2240N have access to the hierarchy 2220. RIA 190 is one example of a co-processor 2240. A texture processing unit (TPU) is another example. A given shader core 2210 may have multiple co-processors and all or a portion of the co-processors may have access to at least a portion of the hierarchy 2220.

In some embodiments, hierarchy 2220 includes a coherence point for a shader memory space that is accessible to a shader core 2210 and its co-processor(s) but is not accessible to other shader cores or their co-processors. Although various embodiments are discussed herein at threadgroup granularity, the granularity at which cores 2210, co-processors 2240, or both access a shader memory space may vary (e.g., SIMD groups, threads, or threadgroups may use the shader memory space to buffer data).

Figure 23:
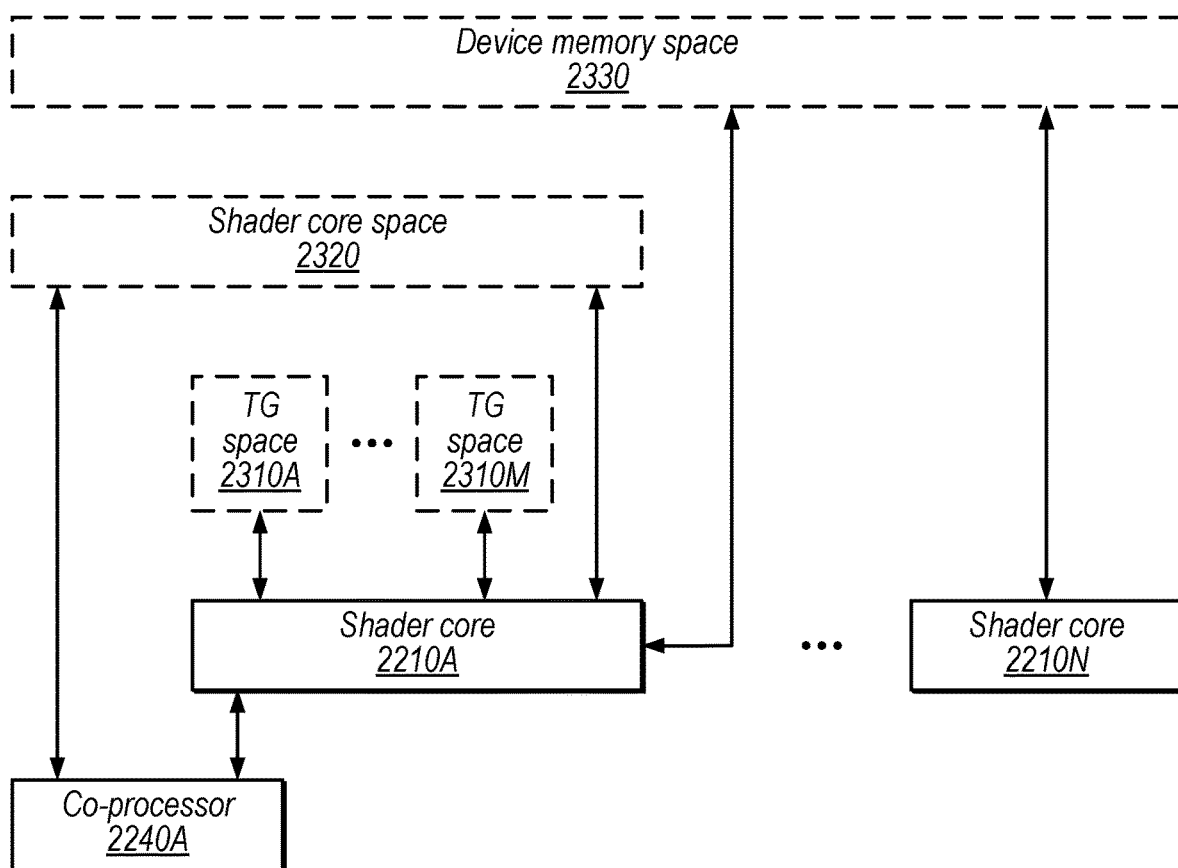
FIG. 23 is a diagram illustrating example threadgroup, shader core, and device memory spaces, according to some embodiments.

FIG. 23 is a diagram illustrating example threadgroup, shader core, and device memory spaces, according to some embodiments. Device memory space 2330, in the illustrated embodiment, is shared by multiple shader cores 2210. In contrast, shader core space 2320, in the illustrated embodiment, is accessible to co-processor 2240A and threadgroups executed by shader core 2210A, but is not accessible to threadgroups executed by other shader cores such as shader core 2210N (although note that shader core 2210N may implement its own shader core space, not explicitly shown). In the illustrated embodiment, threadgroup (TG) memory spaces 2310A-2310M are private memory spaces accessible to a single threadgroup executed by shader core 2210A. In some embodiments, shader core 2210A also implements thread memory spaces (not shown) that are assigned to a single thread.

Figure 24:
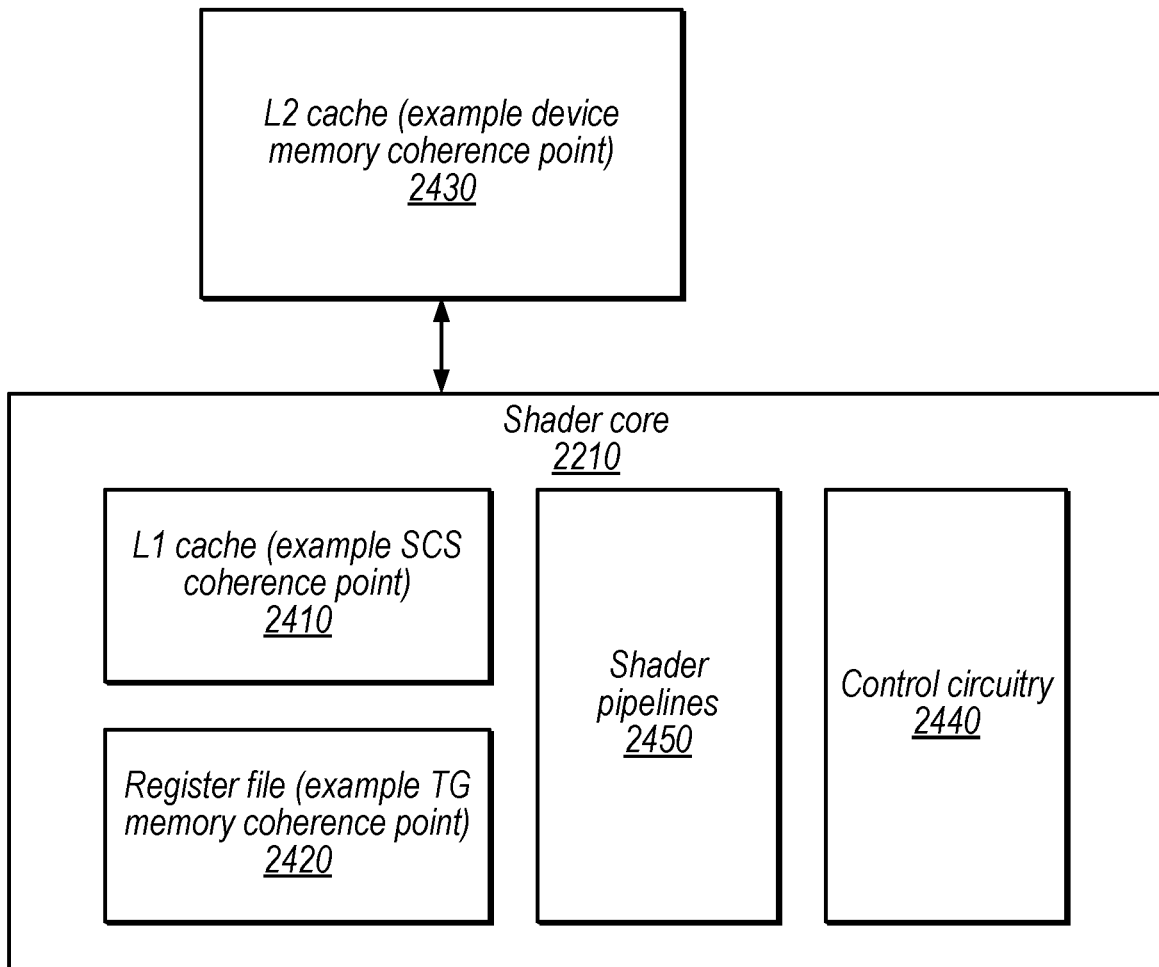
FIG. 24 is a block diagram illustrating example cache organization and coherence points for different memory spaces, according to some embodiments.

FIG. 24 is a block diagram illustrating example cache organization and coherence points for different memory spaces, according to some embodiments. In the illustrated embodiment, shader core 2210 includes an L1 cache 2410, a register file 2420, shader pipelines 2450, and control circuitry 2440. In this example, shader core 2210 is also configured to access a shared L2 cache 2430.

In the illustrated example, the register file 2420 serves as the coherence point for a threadgroup memory space and the L1 cache 2410 serves as the shader core space coherence point. The coherence point is the level at which all entities sharing the memory space (e.g., threadgroups and co-processors for the shader memory space) will see the same cached data. Implementing the shader memory space at the L1 level may reduce memory latency needed to share data (e.g., among threadgroups) by avoiding accesses to higher levels of the memory hierarchy (e.g., to L2 cache 2430).

In unified memory embodiments that do not include a separate register file, the L1 cache may serve as the coherence point for, threadgroup, thread private, and shader core spaces. More generally, the L1 cache may be the coherence point for all memory spaces that are not accessible to circuitry outside of the shader core 2210. In some embodiments, thread private data may be stored in one or more L0 caches (and the L1 cache 2410, as needed). In the illustrated example, the L2 cache serves as the coherence point for a device memory space. In other embodiments, e.g., if the L2 cache is not uniform, a higher level cache such as an L3 cache may serve as a coherence point for device memory space.

Shader pipelines 2450, in some embodiments, are configured to execute instructions of SIMD groups, e.g., using a shared program counter for threads in the SIMD group. These pipelines may include multiple pipeline stages configured to perform operations over multiple clock cycles.

Control circuitry 2440, in some embodiments, is configured to facilitate correct execution of memory access instructions that target different memory spaces. For example, control circuitry may include circuitry to properly execute load, store, allocate, atomic, barrier, etc. instructions that access the shader memory space. For example, loads and stores that access the shader memory space do not store or retrieve data from other spaces. Atomic operations to the shader memory space allow threadgroups to perform memory access operations atomically from the point of view of other threadgroups that can access the space. For example, if the L1 cache is the shader memory space coherence point, a threadgroup may acquire and update one or more L1 cache lines to perform a set of operations atomically. Barrier or fence operations for the shader memory space cause all operations prior to the barrier fence in code that can access the space to complete before operations after the barrier.

The shader core space may be used for various buffering operations in addition to (or in place of) the ray intersection operations described above. For example, thread divergence is a common cause of underutilization in SIMD processors, e.g., for certain graphics workloads. For example, SIMD processors often use predicated execution to handle branch instructions. In predicated execution, both paths after the branch are executed, but threads that did not take the current path are predicated off during its execution. Therefore, if some threads in the same SIMD group are predicated off while others are predicated on, SIMD pipeline hardware may be underutilized.

One way to address such underutilization is to move threads that take different paths to different kernels. This may involve writing result data out to device memory before starting the new kernels, however, which may substantially affect performance. In some embodiments, threads of SIMD groups are broken up (and potentially reformed after executing divergent paths) and new SIMD groups are executed within the same kernel for the different paths. For example, consider the following pseudocode:

```
kernel void divergentTriangleShader ( .... ) {
    // Code Block A
    t = loadTriangleData( );
    p = processTriangle(t);
    if (p < 0) {
        // Code Block B
        subdivide(t);
    }
    else {
        // Code Block C
        softwareRasterize(t, visibilityBuffer);
    }
}
```

In the code example above, the shader may suffer from divergence issues if p<0 is unpredictable, with some threads in the same SIMD group executing code block B (while other threads are predicated off) and other threads in the SIMD group executing code block C. In some embodiments this code is broken up into three different shaders within the same kernel:

```
kernel void processTriangle ( ) {
    t = loadTriangleData( );
    p = processTriangle(t);
// subset of threads queue up work for other kernels at thread granularity,
// to be formed into local simdgroups for immediate execution on local
shader core
    if (p < 0) dispatchWorkitem(t, subdivideTriangleShader);
    else dispatchWorkitem(t, rasterizeTriangleShader);
}
kernel void subdivideTriangle ( ) {
    t = loadTriangleData( );
    subdivide(t);
}
kernel void rasterizeTriangle ( ) {
    softwareRasterize(t, visibilityBuffer);
}
```

In this example, if the processTriangle shader is executed by a SIMD group A, one dynamically-formed SIMD group B may execute the subdivideTriangle path while another dynamically-formed SIMD group C may execute the rasterizeTriangle path. Note that SIMD group B may include threads from multiple different SIMD groups that executed the processTriangle shader (as may SIMD group C).

In some embodiments, this fine-grained local dispatch may use the shader memory space to store intermediate data, rather than sending data up to the coherence point for device memory, for example. For instance, in the example above, SIMD group A may store data in a buffer in shader core space and SIMD groups B and C may read intermediate results from this buffer. Because SIMD groups B and C are in different threadgroups (e.g., because they execute different shaders), shader core space provides a convenient coherence point for sharing data.

Figure 25:
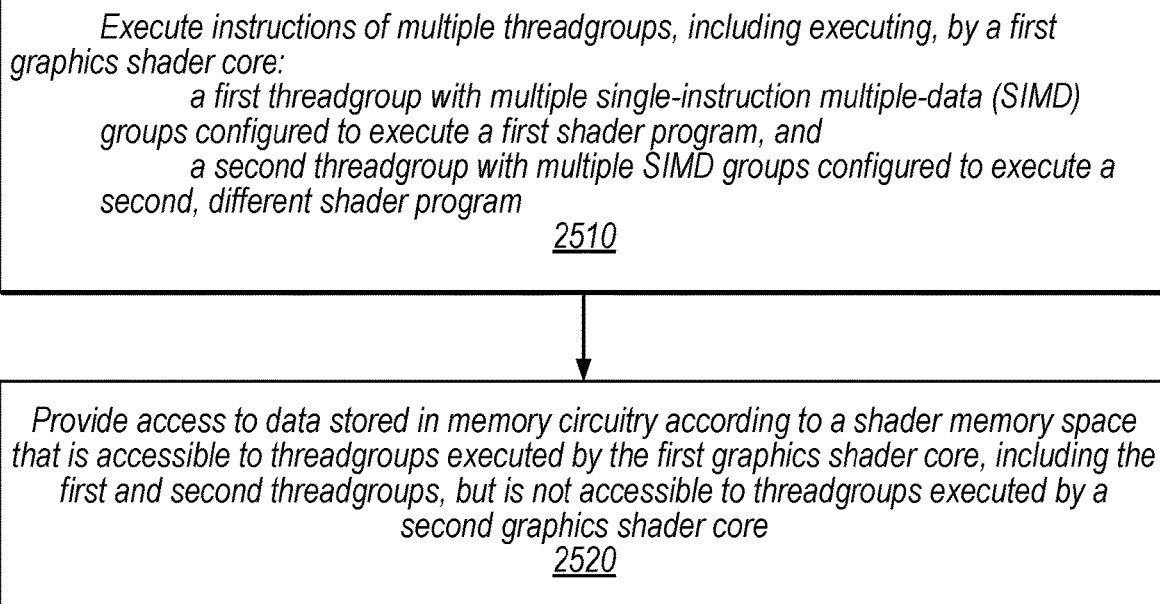
FIG. 25 is a flow diagram illustrating an example method for using a shader memory space, according to some embodiments.

FIG. 25 is a flow diagram illustrating an example method for using a shader memory space, according to some embodiments. The method shown in FIG. 25 may be used in conjunction with any of the computer circuitry, systems, devices, elements, or components disclosed herein, among others. In various embodiments, some of the method elements shown may be performed concurrently, in a different order than shown, or may be omitted. Additional method elements may also be performed as desired.

At 2510, in the illustrated embodiment, first and second graphics shader cores execute instructions of multiple threadgroups. In the illustrated embodiment, this includes executing, by the first graphics shader core, both: a first threadgroup with multiple single-instruction multiple-data (SIMD) groups configured to execute a first shader program, and a second threadgroup with multiple SIMD groups configured to execute a second, different shader program. Note that, in some embodiments, different threadgroups that execute the same shader program may also access the shader memory space. More generally, in some embodiments the shader memory space is accessible to any thread from any SIMD group from any thread group running on the same shader core.

At 2520, in the illustrated embodiment, control circuitry provides access to data stored in memory circuitry according to a shader memory space that is accessible to threadgroups executed by the first graphics shader core, including the first and second threadgroups, but is not accessible to threadgroups executed by the second graphics shader core.

In some embodiments, a first cache in the first graphics shader core (e.g., L1 cache 2410) is a coherence point for the shader memory space and a second, higher-level cache (e.g., L2 cache 2430) in the apparatus is a coherence point for device memory space.

In some embodiments, the control circuitry also provides access to data stored in the memory circuitry according to additional memory spaces with different sharing granularities, including: a threadgroup memory space for the first threadgroup that is accessible to the first threadgroup but not accessible to any other threadgroups, a thread memory space that is accessible to a single thread, and a device memory space that is accessible to threadgroups executed by both the first and second graphics shader cores.

In some embodiments, the shader memory space is also accessible to one or more co-processors for the first graphics shader core. For example, the one or more co-processors include RIA 190. In some embodiments, RIA 190 is configured to: based on an instruction of the first threadgroup (e.g., a clique-A), traverse a spatially organized data structure to determine one or more primitives against which a ray is to be tested for intersection, and initiate the second threadgroup (e.g., a clique-T) to test the one or more primitives against the ray, where both the first threadgroup and the second threadgroup operate on ray information stored in the shader memory space.

In some embodiments, the first graphics shader core is configured to execute load, store, and atomics instructions that target the shader memory space.

In some embodiments, the first graphics shader core is configured to execute a first SIMD group of the first threadgroup to use the shader memory space to store intermediate graphics work at thread granularity to be further processed by threads of a dynamically-formed SIMD group. The dynamically-formed SIMD group may include a set of threads determined to have the same condition result for a conditional control transfer instruction.

Example Device

Referring now to FIG. 26, a block diagram illustrating an example embodiment of a device 2600 is shown. In some embodiments, elements of device 2600 may be included within a system on a chip. In some embodiments, device 2600 may be included in a mobile device, which may be battery-powered. Therefore, power consumption by device 2600 may be an important design consideration. In the illustrated embodiment, device 2600 includes fabric 2610, compute complex 2620 input/output (I/O) bridge 2650, cache/memory controller 2645, graphics unit 150, and display unit 2665. In some embodiments, device 2600 may include other components (not shown) in addition to and/or in place of the illustrated components, such as video processor encoders and decoders, image processing or recognition elements, computer vision elements, etc.

Fabric 2610 may include various interconnects, buses, MUX's, controllers, etc., and may be configured to facilitate communication between various elements of device 2600. In some embodiments, portions of fabric 2610 may be configured to implement various different communication protocols. In other embodiments, fabric 2610 may implement a single communication protocol and elements coupled to fabric 2610 may convert from the single communication protocol to other communication protocols internally.

In the illustrated embodiment, compute complex 2620 includes bus interface unit (BIU) 2625, cache 2630, and cores 2635 and 2640. In various embodiments, compute complex 2620 may include various numbers of processors, processor cores and/or caches. For example, compute complex 2620 may include 1, 2, or 4 processor cores, or any other suitable number. In one embodiment, cache 2630 is a set associative L2 cache. In some embodiments, cores 2635 and/or 2640 may include internal instruction and/or data caches. In some embodiments, a coherency unit (not shown) in fabric 2610, cache 2630, or elsewhere in device 2600 may be configured to maintain coherency between various caches of device 2600. BIU 2625 may be configured to manage communication between compute complex 2620 and other elements of device 2600. Processor cores such as cores 2635 and 2640 may be configured to execute instructions of a particular instruction set architecture (ISA) which may include operating system instructions and user application instructions.

Cache/memory controller 2645 may be configured to manage transfer of data between fabric 2610 and one or more caches and/or memories. For example, cache/memory controller 2645 may be coupled to an L3 cache, which may in turn be coupled to a system memory. In other embodiments, cache/memory controller 2645 may be directly coupled to a memory. In some embodiments, cache/memory controller 2645 may include one or more internal caches.

As used herein, the term "coupled to" may indicate one or more connections between elements, and a coupling may include intervening elements. For example, in FIG. 26, graphics unit 150 may be described as "coupled to" a memory through fabric 2610 and cache/memory controller 2645. In contrast, in the illustrated embodiment of FIG. 26, graphics unit 150 is "directly coupled" to fabric 2610 because there are no intervening elements.

Graphics unit 150 may include one or more processors and/or one or more graphics processing units (GPU's). Graphics unit 150 may receive graphics-oriented instructions, such as OPENGL®, Metal, or DIRECT3D® instructions, for example. Graphics unit 150 may execute specialized GPU instructions or perform other operations based on the received graphics-oriented instructions. Graphics unit 150 may generally be configured to process large blocks of data in parallel and may build images in a frame buffer for output to a display. Graphics unit 150 may include transform, lighting, triangle, and/or rendering engines in one or more graphics processing pipelines. Graphics unit 150 may output pixel information for display images. Programmable shader 160, in various embodiments, may include highly parallel execution cores configured to execute graphics programs, which may include pixel tasks, vertex tasks, and compute tasks (which may or may not be graphics-related).

In some embodiments, graphics unit 150 includes the circuitry discussed herein. In other embodiments, the disclosed circuitry may be implemented in other types of processors, such as CPUs, for example.

Display unit 2665 may be configured to read data from a frame buffer and provide a stream of pixel values for display. Display unit 2665 may be configured as a display pipeline in some embodiments. Additionally, display unit 2665 may be configured to blend multiple frames to produce an output frame. Further, display unit 2665 may include one or more interfaces (e.g., MIPI® or embedded display port (eDP)) for coupling to a user display (e.g., a touchscreen or an external display).

I/O bridge 2650 may include various elements configured to implement: universal serial bus (USB) communications, security, audio, and/or low-power always-on functionality, for example. I/O bridge 2650 may also include interfaces such as pulse-width modulation (PWM), general-purpose input/output (GPIO), serial peripheral interface (SPI), and/or inter-integrated circuit (I2C), for example. Various types of peripherals and devices may be coupled to device 2600 via I/O bridge 2650.

In some embodiments, device 2600 includes network interface circuitry (not explicitly shown), which may be connected to fabric 2610 or I/O bridge 2650. The network interface circuitry may be configured to communicate via various networks, which may be wired, wireless, or both. For example, the network interface circuitry may be configured to communicate via a wired local area network, a wireless local area network (e.g., via WiFi), or a wide area network (e.g., the Internet or a virtual private network). In some embodiments, the network interface circuitry is configured to communicate via one or more cellular networks that use one or more radio access technologies. In some embodiments, the network interface circuitry is configured to communicate using device-to-device communications (e.g., Bluetooth or WiFi Direct), etc. In various embodiments, the network interface circuitry may provide device 2600 with connectivity to various types of other devices and networks.

Example Applications

Turning now to FIG. 27, various types of systems that may include any of the circuits, devices, or system discussed above. System or device 2700, which may incorporate or otherwise utilize one or more of the techniques described herein, may be utilized in a wide range of areas. For example, system or device 2700 may be utilized as part of the hardware of systems such as a desktop computer 2710, laptop computer 2720, tablet computer 2730, cellular or mobile phone 2740, or television 2750 (or set-top box coupled to a television).

Similarly, disclosed elements may be utilized in a wearable device 2760, such as a smartwatch or a health-monitoring device. Smartwatches, in many embodiments, may implement a variety of different functions—for example, access to email, cellular service, calendar, health monitoring, etc. A wearable device may also be designed solely to perform health-monitoring functions, such as monitoring a user's vital signs, performing epidemiological functions such as contact tracing, providing communication to an emergency medical service, etc. Other types of devices are also contemplated, including devices worn on the neck, devices implantable in the human body, glasses or a helmet designed to provide computer-generated reality experiences such as those based on augmented and/or virtual reality, etc.

System or device 2700 may also be used in various other contexts. For example, system or device 2700 may be utilized in the context of a server computer system, such as a dedicated server or on shared hardware that implements a cloud-based service 2770. Still further, system or device 2700 may be implemented in a wide range of specialized everyday devices, including devices 2780 commonly found in the home such as refrigerators, thermostats, security cameras, etc. The interconnection of such devices is often referred to as the "Internet of Things" (IoT). Elements may also be implemented in various modes of transportation. For example, system or device 2700 could be employed in the control systems, guidance systems, entertainment systems, etc. of various types of vehicles 2790.

The applications illustrated in FIG. 27 are merely exemplary and are not intended to limit the potential future applications of disclosed systems or devices. Other example applications include, without limitation: portable gaming devices, music players, data storage devices, unmanned aerial vehicles, etc.

Example Computer-Readable Medium

The present disclosure has described various example circuits in detail above. It is intended that the present disclosure cover not only embodiments that include such circuitry, but also a computer-readable storage medium that includes design information that specifies such circuitry. Accordingly, the present disclosure is intended to support claims that cover not only an apparatus that includes the disclosed circuitry, but also a storage medium that specifies the circuitry in a format that is recognized by a fabrication system configured to produce hardware (e.g., an integrated circuit) that includes the disclosed circuitry. Claims to such a storage medium are intended to cover, for example, an entity that produces a circuit design, but does not itself fabricate the design.

FIG. 28 is a block diagram illustrating an example non-transitory computer-readable storage medium that stores circuit design information, according to some embodiments. In the illustrated embodiment semiconductor fabrication system 2820 is configured to process the design information 2815 stored on non-transitory computer-readable medium 2810 and fabricate integrated circuit 2830 based on the design information 2815.

Non-transitory computer-readable storage medium 2810, may comprise any of various appropriate types of memory devices or storage devices. Non-transitory computer-readable storage medium 2810 may be an installation medium, e.g., a CD-ROM, floppy disks, or tape device; a computer system memory or random access memory such as DRAM, DDR RAM, SRAM, EDO RAM, Rambus RAM, etc.; a non-volatile memory such as a Flash, magnetic media, e.g., a hard drive, or optical storage; registers, or other similar types of memory elements, etc. Non-transitory computer-readable storage medium 2810 may include other types of non-transitory memory as well or combinations thereof. Non-transitory computer-readable storage medium 2810 may include two or more memory mediums which may reside in different locations, e.g., in different computer systems that are connected over a network.

Design information 2815 may be specified using any of various appropriate computer languages, including hardware description languages such as, without limitation: VHDL, Verilog, SystemC, SystemVerilog, RHDL, M, MyHDL, etc. Design information 2815 may be usable by semiconductor fabrication system 2820 to fabricate at least a portion of integrated circuit 2830. The format of design information 2815 may be recognized by at least one semiconductor fabrication system 2820. In some embodiments, design information 2815 may also include one or more cell libraries which specify the synthesis and/or layout of integrated circuit 2830. In some embodiments, the design information is specified in whole or in part in the form of a netlist that specifies cell library elements and their connectivity. Design information 2815, taken alone, may or may not include sufficient information for fabrication of a corresponding integrated circuit. For example, design information 2815 may specify the circuit elements to be fabricated but not their physical layout. In this case, design information 2815 may need to be combined with layout information to actually fabricate the specified circuitry.

Integrated circuit 2830 may, in various embodiments, include one or more custom macrocells, such as memories, analog or mixed-signal circuits, and the like. In such cases, design information 2815 may include information related to included macrocells. Such information may include, without limitation, schematics capture database, mask design data, behavioral models, and device or transistor level netlists. As used herein, mask design data may be formatted according to graphic data system (GDSII), or any other suitable format.

Semiconductor fabrication system 2820 may include any of various appropriate elements configured to fabricate integrated circuits. This may include, for example, elements for depositing semiconductor materials (e.g., on a wafer, which may include masking), removing materials, altering the shape of deposited materials, modifying materials (e.g., by doping materials or modifying dielectric constants using ultraviolet processing), etc. Semiconductor fabrication system 2820 may also be configured to perform various testing of fabricated circuits for correct operation.

In various embodiments, integrated circuit 2830 is configured to operate according to a circuit design specified by design information 2815, which may include performing any of the functionality described herein. For example, integrated circuit 2830 may include any of various elements shown in FIG. 1B, 3A, 6, 7, 14A, 19B, 22A-22B, 24, or 26. Further, integrated circuit 2830 may be configured to perform various functions described herein in conjunction with other components. Further, the functionality described herein may be performed by multiple connected integrated circuits.

As used herein, a phrase of the form "design information that specifies a design of a circuit configured to . . . " does not imply that the circuit in question must be fabricated in order for the element to be met. Rather, this phrase indicates that the design information describes a circuit that, upon being fabricated, will be configured to perform the indicated actions or will include the specified components.

The present disclosure includes references to "an "embodiment" or groups of "embodiments" (e.g., "some embodiments" or "various embodiments"). Embodiments are different implementations or instances of the disclosed concepts. References to "an embodiment," "one embodiment," "a particular embodiment," and the like do not necessarily refer to the same embodiment. A large number of possible embodiments are contemplated, including those specifically disclosed, as well as modifications or alternatives that fall within the spirit or scope of the disclosure.

This disclosure may discuss potential advantages that may arise from the disclosed embodiments. Not all implementations of these embodiments will necessarily manifest any or all of the potential advantages. Whether an advantage is realized for a particular implementation depends on many factors, some of which are outside the scope of this disclosure. In fact, there are a number of reasons why an implementation that falls within the scope of the claims might not exhibit some or all of any disclosed advantages. For example, a particular implementation might include other circuitry outside the scope of the disclosure that, in conjunction with one of the disclosed embodiments, negates or diminishes one or more the disclosed advantages. Furthermore, suboptimal design execution of a particular implementation (e.g., implementation techniques or tools) could also negate or diminish disclosed advantages. Even assuming a skilled implementation, realization of advantages may still depend upon other factors such as the environmental circumstances in which the implementation is deployed. For example, inputs supplied to a particular implementation may prevent one or more problems addressed in this disclosure from arising on a particular occasion, with the result that the benefit of its solution may not be realized. Given the existence of possible factors external to this disclosure, it is expressly intended that any potential advantages described herein are not to be construed as claim limitations that must be met to demonstrate infringement. Rather, identification of such potential advantages is intended to illustrate the type(s) of improvement available to designers having the benefit of this disclosure. That such advantages are described permissively (e.g., stating that a particular advantage "may arise") is not intended to convey doubt about whether such advantages can in fact be realized, but rather to recognize the technical reality that realization of such advantages often depends on additional factors.

Unless stated otherwise, embodiments are non-limiting. That is, the disclosed embodiments are not intended to limit the scope of claims that are drafted based on this disclosure, even where only a single example is described with respect to a particular feature. The disclosed embodiments are intended to be illustrative rather than restrictive, absent any statements in the disclosure to the contrary. The application is thus intended to permit claims covering disclosed embodiments, as well as such alternatives, modifications, and equivalents that would be apparent to a person skilled in the art having the benefit of this disclosure.

For example, features in this application may be combined in any suitable manner. Accordingly, new claims may be formulated during prosecution of this application (or an application claiming priority thereto) to any such combination of features. In particular, with reference to the appended claims, features from dependent claims may be combined with those of other dependent claims where appropriate, including claims that depend from other independent claims. Similarly, features from respective independent claims may be combined where appropriate.

Accordingly, while the appended dependent claims may be drafted such that each depends on a single other claim, additional dependencies are also contemplated. Any combinations of features in the dependent that are consistent with this disclosure are contemplated and may be claimed in this or another application. In short, combinations are not limited to those specifically enumerated in the appended claims.

Where appropriate, it is also contemplated that claims drafted in one format or statutory type (e.g., apparatus) are intended to support corresponding claims of another format or statutory type (e.g., method).

Because this disclosure is a legal document, various terms and phrases may be subject to administrative and judicial interpretation. Public notice is hereby given that the following paragraphs, as well as definitions provided throughout the disclosure, are to be used in determining how to interpret claims that are drafted based on this disclosure.

References to a singular form of an item (i.e., a noun or noun phrase preceded by "a," "an," or "the") are, unless context clearly dictates otherwise, intended to mean "one or more." Reference to "an item" in a claim thus does not, without accompanying context, preclude additional instances of the item. A "plurality" of items refers to a set of two or more of the items.

The word "may" is used herein in a permissive sense (i.e., having the potential to, being able to) and not in a mandatory sense (i.e., must).

The terms "comprising" and "including," and forms thereof, are open-ended and mean "including, but not limited to."

When the term "or" is used in this disclosure with respect to a list of options, it will generally be understood to be used in the inclusive sense unless the context provides otherwise. Thus, a recitation of "x or y" is equivalent to "x or y, or both," and thus covers 1) x but not y, 2) y but not x, and 3) both x and y. On the other hand, a phrase such as "either x or y, but not both" makes clear that "or" is being used in the exclusive sense.

A recitation of "w, x, y, or z, or any combination thereof" or "at least one of . . . w, x, y, and z" is intended to cover all possibilities involving a single element up to the total number of elements in the set. For example, given the set [w, x, y, z], these phrasings cover any single element of the set (e.g., w but not x, y, or z), any two elements (e.g., w and x, but not y or z), any three elements (e.g., w, x, and y, but not z), and all four elements. The phrase "at least one of . . . w, x, y, and z" thus refers to at least one element of the set [w, x, y, z], thereby covering all possible combinations in this list of elements. This phrase is not to be interpreted to require that there is at least one instance of w, at least one instance of x, at least one instance of y, and at least one instance of z.

Various "labels" may precede nouns or noun phrases in this disclosure. Unless context provides otherwise, different labels used for a feature (e.g., "first circuit," "second circuit," "particular circuit," "given circuit," etc.) refer to different instances of the feature. Additionally, the labels "first," "second," and "third" when applied to a feature do not imply any type of ordering (e.g., spatial, temporal, logical, etc.), unless stated otherwise.

The phrase "based on" or is used to describe one or more factors that affect a determination. This term does not foreclose the possibility that additional factors may affect the determination. That is, a determination may be solely based on specified factors or based on the specified factors as well as other, unspecified factors. Consider the phrase "determine A based on B." This phrase specifies that B is a factor that is used to determine A or that affects the determination of A. This phrase does not foreclose that the determination of A may also be based on some other factor, such as C. This phrase is also intended to cover an embodiment in which A is determined based solely on B. As used herein, the phrase "based on" is synonymous with the phrase "based at least in part on."

The phrases "in response to" and "responsive to" describe one or more factors that trigger an effect. This phrase does not foreclose the possibility that additional factors may affect or otherwise trigger the effect, either jointly with the specified factors or independent from the specified factors. That is, an effect may be solely in response to those factors, or may be in response to the specified factors as well as other, unspecified factors. Consider the phrase "perform A in response to B." This phrase specifies that B is a factor that triggers the performance of A, or that triggers a particular result for A. This phrase does not foreclose that performing A may also be in response to some other factor, such as C. This phrase also does not foreclose that performing A may be jointly in response to B and C. This phrase is also intended to cover an embodiment in which A is performed solely in response to B. As used herein, the phrase "responsive to" is synonymous with the phrase "responsive at least in part to." Similarly, the phrase "in response to" is synonymous with the phrase "at least in part in response to."

Within this disclosure, different entities (which may variously be referred to as "units," "circuits," other components, etc.) may be described or claimed as "configured" to perform one or more tasks or operations. This formulation—[entity] configured to [perform one or more tasks]—is used herein to refer to structure (i.e., something physical). More specifically, this formulation is used to indicate that this structure is arranged to perform the one or more tasks during operation. A structure can be said to be "configured to" perform some task even if the structure is not currently being operated. Thus, an entity, described or recited as being "configured to" perform some task refers to something physical, such as a device, circuit, a system having a processor unit and a memory storing program instructions executable to implement the task, etc. This phrase is not used herein to refer to something intangible.

In some cases, various units/circuits/components may be described herein as performing a set of task or operations. It is understood that those entities are "configured to" perform those tasks/operations, even if not specifically noted.

The term "configured to" is not intended to mean "configurable to." An unprogrammed FPGA, for example, would not be considered to be "configured to" perform a particular function. This unprogrammed FPGA may be "configurable to" perform that function, however. After appropriate programming, the FPGA may then be said to be "configured to" perform the particular function.

For purposes of United States patent applications based on this disclosure, reciting in a claim that a structure is "configured to" perform one or more tasks is expressly intended not to invoke 35 U.S.C. § 112(f) for that claim element. Should Applicant wish to invoke Section 112(f) during prosecution of a United States patent application based on this disclosure, it will recite claim elements using the "means for" [performing a function] construct.

Different "circuits" may be described in this disclosure. These circuits or "circuitry" constitute hardware that includes various types of circuit elements, such as combinatorial logic, clocked storage devices (e.g., flip-flops, registers, latches, etc.), finite state machines, memory (e.g., random-access memory, embedded dynamic random-access memory), programmable logic arrays, and so on. Circuitry may be custom designed, or taken from standard libraries. In various implementations, circuitry can, as appropriate, include digital components, analog components, or a combination of both. Certain types of circuits may be commonly referred to as "units" (e.g., a decode unit, an arithmetic logic unit (ALU), functional unit, memory management unit (MMU), etc.). Such units also refer to circuits or circuitry.

The disclosed circuits/units/components and other elements illustrated in the drawings and described herein thus include hardware elements such as those described in the preceding paragraph. In many instances, the internal arrangement of hardware elements within a particular circuit may be specified by describing the function of that circuit. For example, a particular "decode unit" may be described as performing the function of "processing an opcode of an instruction and routing that instruction to one or more of a plurality of functional units," which means that the decode unit is "configured to" perform this function. This specification of function is sufficient, to those skilled in the computer arts, to connote a set of possible structures for the circuit.

In various embodiments, as discussed in the preceding paragraph, circuits, units, and other elements defined by the functions or operations that they are configured to implement, The arrangement and such circuits/units/components with respect to each other and the manner in which they interact form a microarchitectural definition of the hardware that is ultimately manufactured in an integrated circuit or programmed into an FPGA to form a physical implementation of the microarchitectural definition. Thus, the microarchitectural definition is recognized by those of skill in the art as structure from which many physical implementations may be derived, all of which fall into the broader structure described by the microarchitectural definition. That is, a skilled artisan presented with the microarchitectural definition supplied in accordance with this disclosure may, without undue experimentation and with the application of ordinary skill, implement the structure by coding the description of the circuits/units/components in a hardware description language (HDL) such as Verilog or VHDL. The HDL description is often expressed in a fashion that may appear to be functional. But to those of skill in the art in this field, this HDL description is the manner that is used transform the structure of a circuit, unit, or component to the next level of implementational detail. Such an HDL description may take the form of behavioral code (which is typically not synthesizable), register transfer language (RTL) code (which, in contrast to behavioral code, is typically synthesizable), or structural code (e.g., a netlist specifying logic gates and their connectivity). The HDL description may subsequently be synthesized against a library of cells designed for a given integrated circuit fabrication technology, and may be modified for timing, power, and other reasons to result in a final design database that is transmitted to a foundry to generate masks and ultimately produce the integrated circuit. Some hardware circuits or portions thereof may also be custom-designed in a schematic editor and captured into the integrated circuit design along with synthesized circuitry. The integrated circuits may include transistors and other circuit elements (e.g. passive elements such as capacitors, resistors, inductors, etc.) and interconnect between the transistors and circuit elements. Some embodiments may implement multiple integrated circuits coupled together to implement the hardware circuits, and/or discrete elements may be used in some embodiments. Alternatively, the HDL design may be synthesized to a programmable logic array such as a field programmable gate array (FPGA) and may be implemented in the FPGA. This decoupling between the design of a group of circuits and the subsequent low-level implementation of these circuits commonly results in the scenario in which the circuit or logic designer never specifies a particular set of structures for the low-level implementation beyond a description of what the circuit is configured to do, as this process is performed at a different stage of the circuit implementation process.

The fact that many different low-level combinations of circuit elements may be used to implement the same specification of a circuit results in a large number of equivalent structures for that circuit. As noted, these low-level circuit implementations may vary according to changes in the fabrication technology, the foundry selected to manufacture the integrated circuit, the library of cells provided for a particular project, etc. In many cases, the choices made by different design tools or methodologies to produce these different implementations may be arbitrary.

Moreover, it is common for a single implementation of a particular functional specification of a circuit to include, for a given embodiment, a large number of devices (e.g., millions of transistors). Accordingly, the sheer volume of this information makes it impractical to provide a full recitation of the low-level structure used to implement a single embodiment, let alone the vast array of equivalent possible implementations. For this reason, the present disclosure describes structure of circuits using the functional shorthand commonly employed in the industry.

What is claimed is:

1. An apparatus, comprising:
   first and second graphics shader cores configured to execute instructions for multiple threadgroups, wherein the first graphics shader core is configured to execute:
      a first threadgroup that includes multiple single-instruction multiple-data (SIMD) groups configured to execute a first shader program for multiple threads; and
      a second threadgroup that includes multiple SIMD groups configured to execute a second, different shader program for multiple threads;
   memory circuitry;
   control circuitry, wherein the control circuitry is configured to:
      provide access to data stored in the memory circuitry according to a shader memory space that is accessible to threadgroups executed by the first graphics shader core, including the first and second threadgroups, but is not accessible to threadgroups executed by the second graphics shader core; and
      provide access to data stored in the memory circuitry according to multiple threadgroup spaces that are assigned to a given threadgroup and not accessible to other threadgroups; and
   ray intersection circuitry configured to:
      based on a ray intersect instruction of the first threadgroup, traverse a spatially organized data structure to determine one or more primitives against which a ray is to be tested for intersection; and
      initiate at least a portion of the second threadgroup to test the one or more primitives against the ray, wherein both the first threadgroup and second threadgroup access the shader memory space for ray information.

2. The apparatus of claim 1, wherein a first cache in the first graphics shader core is a coherence point for the shader memory space and a second, higher-level cache in the apparatus is a coherence point for device memory space.

3. The apparatus of claim 1, wherein the control circuitry is further configured to provide access to data stored in the memory circuitry according to the following memory spaces:
   a threadgroup memory space for the first threadgroup that is accessible to the first threadgroup but not accessible to any other threadgroups;
   a thread memory space that is accessible to a single thread; and
   a device memory space that is accessible to threadgroups executed by both the first and second graphics shader cores.

4. The apparatus of claim 1, wherein the first threadgroup stores ray data to the shader memory space and the second threadgroup reads ray data from the shader memory space.

5. The apparatus of claim 1, wherein the first graphics shader core is configured to execute load, store, and atomics instructions that target the shader memory space.

6. The apparatus of claim 1, wherein the first graphics shader core is configured to execute a first SIMD group of the first threadgroup to use the shader memory space to store intermediate graphics work at thread granularity to be further processed by threads of a dynamically-formed SIMD group.

7. The apparatus of claim 6, wherein the dynamically-formed SIMD group includes a set of threads determined to have the same condition result for a conditional control transfer instruction.

8. A method, comprising:
   executing, by first and second graphics shader cores, instructions of multiple threadgroups, including executing, by the first graphics shader core:
      a first threadgroup that includes multiple single-instruction multiple-data (SIMD) groups configured to execute a first shader program; and
      a second threadgroup that includes multiple SIMD groups configured to execute a second, different shader program; and
   providing, by control circuitry, access to data stored in memory circuitry according to a shader memory space that is accessible to threadgroups executed by the first graphics shader core, including the first and second threadgroups, but is not accessible to threadgroups executed by the second graphics shader core;
   providing, by the control circuitry, access to data stored in the memory circuitry according to multiple threadgroup spaces that are dedicated to a given threadgroup and not accessible to other threadgroups;
   traversing, based on a ray intersect instruction of the first threadgroup, a spatially organized data structure to determine one or more primitives against which a ray is to be tested for intersection; and
   initiating at least a portion of the second threadgroup to test the one or more primitives against the ray, wherein both the first threadgroup and second threadgroup access the shader memory space for ray information.

9. The method of claim 8, wherein the first threadgroup stores ray data to the shader memory space and the second threadgroup reads ray data from the shader memory space.

10. The method of claim 8, wherein a first SIMD group of the first threadgroup uses the shader memory space to store intermediate graphics work at thread granularity to be further processed by threads of a dynamically-formed SIMD group; and
    wherein the dynamically-formed SIMD group includes a set of threads determined to have the same condition result for a conditional control transfer instruction.

11. The method of claim 8, wherein the providing includes providing access to data stored in the memory circuitry according to the following memory spaces:
   a threadgroup memory space for the first threadgroup that is accessible to the first threadgroup but not accessible to any other threadgroups;
   a thread memory space that is accessible to a single thread; and
   a device memory space that is accessible to threadgroups executed by both the first and second graphics shader cores.

12. The method of claim 11, further comprising:
   enforcing coherence for the shader memory space at a first cache in the first graphics shader core; and
   enforcing coherence for the device memory space at a second, higher-level cache.

13. The method of claim 8, further comprising executing, by the first graphics shader core, load, store, and atomics instructions that target the shader memory space.

14. A non-transitory computer readable storage medium having stored thereon design information that specifies a design of at least a portion of a hardware integrated circuit in a format recognized by a semiconductor fabrication system that is configured to use the design information to produce the circuit according to the design, wherein the design information specifies that the circuit includes:
    first and second graphics shader cores configured to execute instructions for multiple threadgroups, wherein the first graphics shader core is configured to execute:
        a first threadgroup that includes multiple single-instruction multiple-data (SIMD) groups configured to execute a first shader program; and
        a second threadgroup that includes multiple SIMD groups configured to execute a second, different shader program;
    memory circuitry; and
    control circuitry, wherein the control circuitry is configured to:
        provide access to data stored in the memory circuitry according to a shader memory space that is accessible to threadgroups executed by the first graphics shader core, including the first and second threadgroups, but is not accessible to threadgroups executed by the second graphics shader core; and
        provide access to data stored in the memory circuitry according to multiple threadgroup spaces that are dedicated to a given threadgroup and not accessible to other threadgroups; and
    ray intersection circuitry configured to:
        based on a ray intersect instruction of the first threadgroup, traverse a spatially organized data structure to determine one or more primitives against which a ray is to be tested for intersection; and
        initiate at least a portion of the second threadgroup to test the one or more primitives against the ray, wherein both the first threadgroup and second threadgroup access the shader memory space for ray information.

15. The non-transitory computer readable storage medium of claim 14, wherein a first cache in the first graphics shader core is a coherence point for the shader memory space and a second, higher-level cache shared by the second graphics shader core is a coherence point for device memory space.

16. The non-transitory computer readable storage medium of claim 14, wherein the control circuitry is further configured to provide access to data stored in the memory circuitry according to the following memory spaces:
    a threadgroup memory space for the first threadgroup that is accessible to the first threadgroup but not accessible to any other threadgroups;
    a thread memory space that is accessible to a single thread; and
    a device memory space that is accessible to threadgroups executed by both the first and second graphics shader cores.

17. The non-transitory computer readable storage medium of claim 14, wherein the first threadgroup stores ray data to the shader memory space and the second threadgroup reads ray data from the shader memory space.

18. The non-transitory computer readable storage medium of claim 14, wherein the first graphics shader core is configured to execute load, store, and atomics instructions that target the shader memory space.

19. The non-transitory computer readable storage medium of claim 14, wherein the first graphics shader core is configured to execute a first SIMD group of the first threadgroup to use the shader memory space to store intermediate graphics work at thread granularity to be further processed by threads of a dynamically-formed SIMD group.

20. The non-transitory computer readable storage medium of claim 19, wherein the dynamically-formed SIMD group includes a set of threads determined to have the same condition result for a conditional control transfer instruction.

* * * * *